United States Patent
Sullivan et al.

(10) Patent No.: US 12,391,632 B2
(45) Date of Patent: Aug. 19, 2025

(54) MIXED METAL OXIDE CATALYST CONTAINING TANTALUM FOR ODH OF ETHANE

(71) Applicant: NOVA CHEMICALS (INTERNATIONAL) S.A., Fribourg (CH)

(72) Inventors: David Sullivan, Calgary (CA); Vasily Simanzhenkov, Calgary (CA); Yoonhee Kim, Calgary (CA); Marie Barnes, Calgary (CA); Bolaji Olayiwola, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 74 days.

(21) Appl. No.: 18/275,859

(22) PCT Filed: Feb. 3, 2022

(86) PCT No.: PCT/IB2022/050945
§ 371 (c)(1),
(2) Date: Aug. 4, 2023

(87) PCT Pub. No.: WO2022/167967
PCT Pub. Date: Aug. 11, 2022

(65) Prior Publication Data
US 2024/0034701 A1 Feb. 1, 2024

Related U.S. Application Data

(60) Provisional application No. 63/145,943, filed on Feb. 4, 2021.

(51) Int. Cl.
*C07C 5/48* (2006.01)
*B01J 21/04* (2006.01)
(Continued)

(52) U.S. Cl.
CPC ............... *C07C 5/48* (2013.01); *B01J 21/04* (2013.01); *B01J 21/063* (2013.01); *B01J 21/066* (2013.01);
(Continued)

(58) Field of Classification Search
CPC ... C07C 5/48; C07C 2523/20; C07C 2523/22; C07C 2523/28; C07C 2523/32;
(Continued)

(56) References Cited

U.S. PATENT DOCUMENTS 10,350,582 B2 * 7/2019 Simanzhenkov ...... B01J 23/002
10,589,258 B2 3/2020 Simanzhenkov et al.
(Continued)

FOREIGN PATENT DOCUMENTS

| CN | 108855118 A | 11/2018 |
| CN | 110234431 A | 9/2019 |
| TW | 201041839 A | 12/2010 |

OTHER PUBLICATIONS

DeSanto et al., "Comparison of MoVTaTeO and MoVNbTeO M1 crystal chemistry," Topics in Catalysis, Jul. 2006, 38(1-3), pp. 31-40.
(Continued)

*Primary Examiner* — Ali Z Fadhel
(74) *Attorney, Agent, or Firm* — Fish & Richardson P.C.

(57) ABSTRACT

A catalyst, useful for oxidative dehydrogenation of ethane, comprising molybdenum, vanadium, tellurium, tantalum, and oxygen, prepared using a stage hydrothermal synthesis procedure, is provided. The catalyst comprises from 30 to 50 wt. % amorphous content and may be combined with a support/carrier material to form a catalyst material. The described catalysts and catalyst materials demonstrate high selectivity for ethylene at higher temperatures, show little to no decline in conversion and selectivity over time, and do
(Continued)

not appear to be sensitive to low residual oxygen concentrations.

19 Claims, 11 Drawing Sheets

(51) Int. Cl.
| | |
|---|---|
| *B01J 21/06* | (2006.01) |
| *B01J 21/08* | (2006.01) |
| *B01J 21/12* | (2006.01) |
| *B01J 23/00* | (2006.01) |
| *B01J 27/057* | (2006.01) |
| *B01J 35/61* | (2024.01) |
| *B01J 35/63* | (2024.01) |
| *B01J 37/04* | (2006.01) |
| *B01J 37/08* | (2006.01) |

(52) U.S. Cl.
CPC ............... *B01J 21/08* (2013.01); *B01J 21/12* (2013.01); *B01J 23/002* (2013.01); *B01J 27/0576* (2013.01); *B01J 35/612* (2024.01); *B01J 35/633* (2024.01); *B01J 37/04* (2013.01); *B01J 37/08* (2013.01); *B01J 2523/55* (2013.01); *B01J 2523/57* (2013.01); *B01J 2523/64* (2013.01); *B01J 2523/68* (2013.01); *C07C 2523/20* (2013.01); *C07C 2523/22* (2013.01); *C07C 2523/28* (2013.01); *C07C 2523/32* (2013.01)

(58) Field of Classification Search
CPC ............ C07C 2521/02; C07C 2521/06; C07C 2523/02; C07C 2523/04; C07C 2523/745; C07C 2523/887; C07C 2527/057; B01J 21/04; B01J 21/063; B01J 21/066; B01J 21/08; B01J 21/12; B01J 23/002; B01J 27/0576; B01J 35/612; B01J 35/633; B01J 37/04; B01J 37/08; B01J 2523/55; B01J 2523/57; B01J 2523/64; B01J 2523/68; B01J 35/70; B01J 35/80; B01J 35/45; B01J 2235/00; B01J 2235/10; B01J 2235/15; B01J 2235/30; B01J 2523/00; B01J 37/031; B01J 23/28; Y02P 20/52

See application file for complete search history.

(56) References Cited

U.S. PATENT DOCUMENTS

| | | | |
|---|---|---|---|
| 2010/0222623 A1* | 9/2010 | Ryan .................. | C07C 5/48 585/654 |
| 2010/0255986 A1* | 10/2010 | Gaffney ............... | B01J 37/0009 502/312 |
| 2020/0061583 A1 | 2/2020 | Mestl et al. | |

OTHER PUBLICATIONS

Grasselli et.al., "Active centers, catalytic behavior, symbiosis and redox properties of MoV(Nb,Ta)TeO ammoxidation catalysts," Topics in Catalysis, Jul. 2006, 38(1-3), pp. 7-16.

PCT International Preliminary Report on Patentability in International Appln. No. PCT/IB2022/050945, mailed on Aug. 3, 2023, 6 pages.

PCT International Search Report and Written Opinion in International Appln. No. PCT/IB2022/050945, mailed on May 6, 2022, 9 pages.

O'Connor et al., "Application of the Rietveld Refinement Procedure in Assaying Powdered Mixtures," Powder Diffraction, Mar. 1988, 3(1), pp. 2-6.

Chinese Office Action in Chinese Appln. No. 202280013038.5, mailed on Jun. 26, 2025, with English Translation, 16 pages.

Melzer et al., "Design and synthesis of highly active MoVTeNb oxides for ethane oxidative dehydrogenation," Nature Communications, 2019, 10(4012): 1-9.

* cited by examiner

MIXED METAL OXIDE CATALYST CONTAINING TANTALUM FOR ODH OF ETHANE

CROSS-REFERENCE TO RELATED APPLICATIONS

This application is a National Stage Application under 35 U.S.C. § 371 and claims the benefit of International Application No. PCT/IB2022/050945, filed Feb. 3, 2022, which claims priority to U.S. Provisional Application No. 63/145,943 filed on Feb. 4, 2021, the entire contents of which are hereby incorporated by reference.

TECHNICAL FIELD

The present disclosure relates generally to catalysts and systems for oxidative dehydrogenation (ODH). More specifically, the catalyst contains molybdenum (Mo), vanadium (V), tellurium (Te), tantalum (Ta), and oxygen (O).

BACKGROUND ART

Olefins like ethylene, propylene, and butylene, are basic building blocks for a variety of commercially valuable polymers. Since naturally occurring sources of olefins do not exist in commercial quantities, polymer producers rely on methods for converting the more abundant lower alkanes into olefins. The method of choice for today's commercial scale producers is steam cracking, a highly endothermic process where steam-diluted alkanes are subjected very briefly to a temperature of at least 800° C. The fuel demand to produce the required temperatures and the need for equipment that can withstand that temperature add significantly to the overall cost. In addition, the high temperature promotes the formation of coke, which accumulates within the system, resulting in the need for costly periodic reactor shutdown for maintenance and coke removal.

Selective oxidation processes, such as oxidative dehydrogenation (ODH), are an alternative to steam cracking that are exothermic and produce little or no coke. In ODH, a lower alkane, such as ethane, is mixed with oxygen in the presence of a catalyst and optionally an inert diluent, such as carbon dioxide, methane, nitrogen or steam, at temperatures as low as 300° C. to produce the corresponding alkene. Various other oxidation products may be produced in this process, including carbon dioxide and acetic acid, among others. ODH suffers from lower conversion rates when compared to steam cracking, a fact that when combined with lower selectivity and the risk of thermal explosion due to mixing of a hydrocarbon with oxygen, may have prevented ODH from achieving widespread commercial implementation.

There is a need for a catalyst for an ODH of ethane process with high ethylene selectivity. It has been observed that the MoVNbTeO$_x$ catalyst used in ODH processes exhibits permanent activity and selectivity loss over time at elevated ODH temperatures. The robustness of the catalyst to oxygen-depleted ODH conditions has also been tested and it has been found that while the catalyst activity would recover completely after air regeneration cycles, the selectivity would only partially recover, falling below 90% at 25% conversion. It was shown that running the reactor at a low temperature of 350° C. with low space velocity caused a smaller loss in selectivity of the catalyst as compared to subjecting the catalyst to temperatures above 360° C. Therefore, applying the MoVNbTeO$_x$ catalyst in a commercial ODH process would require the plant to operate at both lower temperature and GHSV in order to maintain high catalyst performance. These process restrictions would require a larger reactor volume size (higher CAPEX), a narrower temperature operating window, and ultimately more difficult operation of the reactor.

SUMMARY OF INVENTION

The present disclosure relates to a mixed metal oxide catalyst for the oxidative dehydrogenation of ethane comprising Mo, V, Te, and Ta, that provides high conversion and selectivity. The catalyst has the formula:

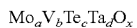

$$Mo_aV_bTe_cTa_dO_x$$

wherein:
  a is 1.0;
  b is about 0.35 to about 1.0;
  c is about 0.1 to about 1.0;
  d is about 0.06 to about 1.0; and
  x is a number to at least satisfy the valence of the catalyst; and
wherein the amorphous content of the catalyst is about 30 wt. % to about 50 wt. %.

Catalysts prepared using a staged hydrothermal synthesis, as described herein, with preparation and mixing of aqueous precursor salt solutions, hydrothermal baking of the final solution, and calcination demonstrate high selectivity for ethylene at higher temperatures.

Further, the Mo$_a$V$_b$Te$_c$Ta$_d$O$_x$ catalyst, when used in an ethane oxidative dehydrogenati process, show little to no decline in conversion and selectivity over time and are not sensitive to low oxygen concentrations.

Also described herein is a process for the oxidative dehydrogenation of ethane wherein the Mo$_a$V$_b$Te$_c$Ta$_d$O$_x$ catalyst is contacted with ethane in the presence of oxygen in a reactor to produce an effluent comprising ethylene.

DESCRIPTION OF EMBODIMENTS

Figure 1:
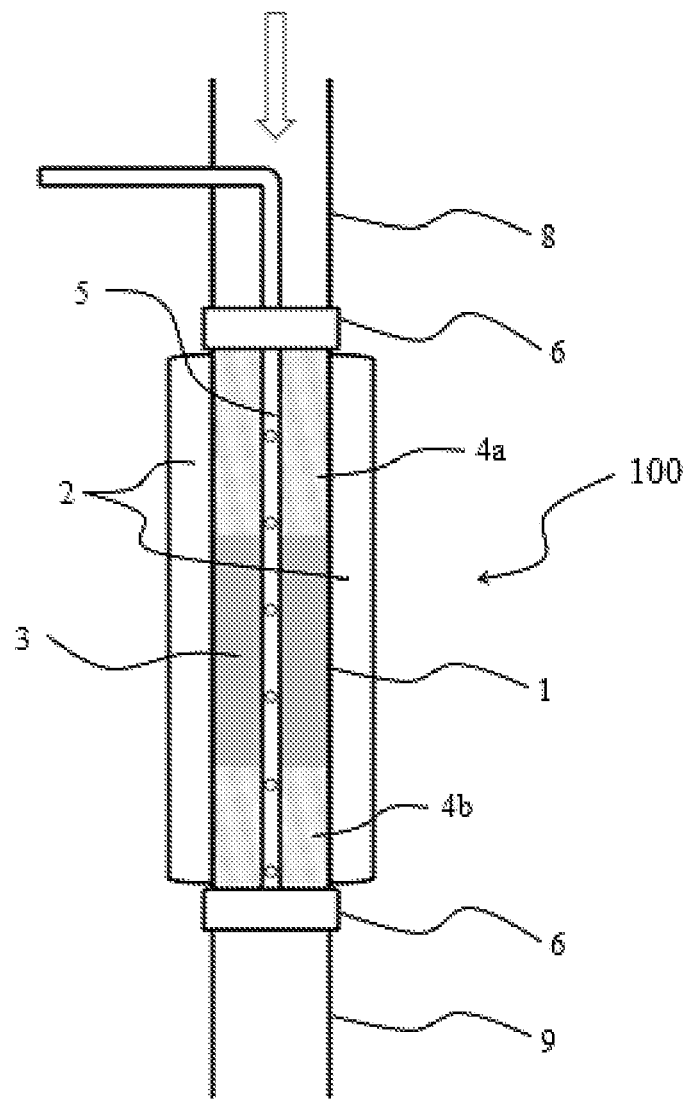
FIG. 1 shows a cross section schematic of a microreactor unit (MRU) setup.

Selective oxidation (SO) is generally used in ODH reactions to form ethylene, or other alpha-olefins, from ethane. Embodiments described herein provide a catalyst system for a selective oxidation reaction.

Provided herein is a MoVTeTaO$_x$ catalyst that is useful for an ODH of ethane process that has high ethylene selectivity. In some embodiments, the catalyst exhibits favorable process performance characteristics. In some embodiments, the MoVTeTaO$_x$ catalyst exhibits improved properties as compared to the MoVTeNbO$_x$ catalyst known in the art. In some embodiments, the MoVTeTaO$_x$ catalyst is stable at operation above 400° C., maintaining high activity and selectivity. In some embodiments, the catalyst maintains high activity and selectivity after a slight initial activity loss. In some embodiments, the slight initial activity loss is attributed to catalyst equilibration. The enhanced stability is beneficial because it provides the option to operate at higher reactor temperatures than previously considered.

In some embodiments, the MoVTeTaO$_x$ catalyst exhibits high tolerance to low residual oxygen conditions while producing high conversion and selectivity. This is beneficial because it should allow for more conversion and in turn higher ethylene yields without negative impact to the catalyst life. Lower residual oxygen in a resulting gaseous product stream may also be associated with reduced oxygen separation requirements downstream of an ODH process.

In some embodiments, use of the MoVTeTaO$_x$ catalyst results in low acetic acid production, which allows high ethylene selectivity. High ethylene selectivity means reduced CAPEX & OPEX for acetic acid purification that would be part of downstream processing in an ODH plant. It also means the sale of acetic acid product should be more manageable as the North American market demand for acetic acid is very small (34 kTA).

Thus, provided herein is an ODH catalyst that exhibits improved properties as compared to other ODH catalysts containing tantalum that have been disclosed in the art. For example, the catalyst of the present disclosure can operate at a much higher temperature (resulting in higher conversion) without comprising selectivity; the catalyst of the present disclosure is not deactivated by low oxygen concentration (can almost exhaust O$_2$ in the product stream); the catalyst of the present disclosure produces low levels of acetic acid; the catalyst of the present disclosure is prepared using a staged hydrothermal synthesis as opposed to a "single pot" synthesis; the catalyst of the present disclosure comprises a much higher M1 phase compared to previously disclosed tantalum containing catalysts; and the catalyst of the present disclosure has a distinctive X-ray diffraction (XRD) profile.

Provided herein is an oxidative dehydrogenation catalyst material that includes molybdenum (Mo), vanadium (V), tellurium (Te), tantalum (Ta), and oxygen (O). The catalyst is represented by the formula MoVTeTaO$_x$. In some embodiments, the catalyst has the formula Mo$_a$V$_b$Te$_c$Ta$_d$O$_x$, wherein a is 1.0; b is about 0.35 to about 1.0; c is about 0.1 to about 1.0; d is about 0.06 to about 1.0; and x is a number to at least satisfy the valence of the catalyst. In some embodiments, the catalyst has the formula Mo$_1$V$_{0.35-1.0}$Te$_{0.1-1.0}$Ta$_{0.06-1.0}$. In some embodiments, the catalyst has the formula Mo$_1$V$_{0.39-0.49}$Te$_{0.12-0.17}$Ta$_{0.06-0.15}$. In some embodiments, the catalyst has the formula Mo$_1$V$_{0.49}$Te$_{0.15}$Ta$_{0.07}$. In some embodiments, the amorphous content of the catalyst is about 30 wt. % to about 50 wt. %.

In some embodiments, a is 1.0.

In some embodiments, b is about 0.35 to about 1.0. In some embodiments, b is about 0.35 to about 0.75. In some embodiments, b is about 0.39 to about 0.49. In some embodiments, b is about 0.45 to about 0.7. In some embodiments, b is about 0.49.

In some embodiments, c is about 0.1 to about 1.0. In some embodiments, c is about 0.1 to about 0.2. In some embodiments, c is about 0.12 to about 0.17. In some embodiments, c is about 0.14 to about 0.18. In some embodiments, c is about 0.15.

In some embodiments, d is about 0.06 to about 1.0. In some embodiments, d is about 0.06 to about 0.15. In some embodiments, d is about 0.06 to about 0.15. In some embodiments, d is about 0.06 to about 0.10. In some embodiments, d is about 0.07.

In some embodiments, x is the number of oxygen atoms necessary to at least satisfy the valence of the catalyst.

In some embodiments, the amorphous content of the catalyst is about 30 wt. % to about 50 wt. %. In some embodiments, the amorphous content of the catalyst is about 30 wt. % to about 40 wt. %. In some embodiments, the amorphous content of the catalyst is about 33 wt. % to about 36 wt. %. In some embodiments, the amorphous content of the catalyst is about 34 wt. % to about 35 wt. %.

It is preferable that the MoVTeTaO$_x$ catalyst is prepared using a synthesis procedure involving 3 general steps. The first step includes the preparation of aqueous solutions of the catalyst precursor salts for each of the elements molybdenum, vanadium, tellurium, and tantalum. The molybdenum and tellurium components may be prepared as a combined aqueous preparation to which the vanadium aqueous preparation may be added. The tantalum aqueous preparation may then be added to form a final aqueous composition. The second step involves hydrothermal baking of the final aqueous composition to form a slurry which may be filtered and rinsed to isolate a solid catalyst. The final step includes calcination of the solid catalyst. The staged hydrothermal method described is distinct from known "single pot" synthesis procedures where all the components are added at the same time in a single pot to form an in situ product.

The described MoVTeTaO$_x$ catalyst, when analyzed using X-Ray Diffractometry (XRD), demonstrates a pattern with distinct peaks. In some embodiments, the XRD pattern comprises peaks at °2θ values of 22.2±0.2, 26.7±0.2, and 28.3±0.2. In some embodiments, the XRD pattern comprises peaks at °2θ values of 7.9±0.2, 9.0 0.2, 22.2±0.2, 23.0±0.2, 25.0±0.2, 26.7±0.2, and 28.3±0.2.

Also provided herein is a catalyst material that includes a catalyst, such as a catalyst of the present disclosure, and a catalyst support or carrier. Some supports are particularly suitable for the catalyst in that they are chemically compatible and have no substantial impact on ethylene selectivity. Other supports may be less compatible, meaning they may lead to substantial reduction of catalyst performance such as a reduction in ethylene selectivity. Consequently, not just any support can be chosen; the support should be selected in a judicious matter based off both short-term and longer-term catalysis performance testing. In some embodiments, there is an emphasis on long-term testing showing no loss of selectivity with time on steam (for example, time on stream (TOS) of >48 hours). In some embodiments, the catalyst support or carrier is selected from the group consisting of precipitated synthetic silica, fumed synthetic silica, silica-alumina, α-alumina, and anatase titania. In some embodiments, the catalyst support or carrier is precipitated synthetic silica. In some embodiments, the catalyst support or carrier is fumed silica Also provide herein is a process for the oxidative dehydrogenation of ethane, the process comprising contacting a gaseous feed comprising ethane and oxygen with a catalyst in a reactor to produce an effluent comprising ethylene, wherein the catalyst has the formula:

$$Mo_aV_bTe_cTa_dO_x$$

wherein:
a is 1.0;
b is about 0.35 to about 1.0;
c is about 0.1 to about 1.0;
d is about 0.06 to about 1.0; and
x is a number to at least satisfy the valence of the catalyst; and wherein the amorphous content of the catalyst is about 30 wt. % to about 50 wt. %.

Suitable reactors for use with the catalyst and process described herein include fixed bed reactors where the catalyst is immobilized in a catalyst bed. Also particularly suitable for use with the catalyst and process described herein are shell-and-tube reactors, including, but not limited to, shell-and-tube reactors with molten salt cooling capabilities.

The ability of the catalyst in an ethane ODH process to convert ethane into ethylene can be assessed by determination of conversion and selectivity. Conversion is described in terms of the temperature at which a specific molar percentage of ethane is converted to ethylene and associated byproducts. Selectivity is described in terms of what percentage of converted ethane is converted into ethylene (or a specific byproduct). Conversion typically increases as the temperature increases. Unfortunately, for some ODH catalysts higher temperatures are associated with lower selectivity to ethylene, and in some cases, if the temperature is high enough, conversion rates actually decrease and the catalyst may even become irreversibly deactivated. Commercial success may depend on using a catalyst that operates at higher temperatures while maintaining a selectivity to ethylene of greater than 90%. Maximizing conversion while maintaining selectivity would be extremely beneficial.

In some embodiments, the catalyst described, when used in a process for oxidative dehydrogenation of ethane, demonstrates conversion of 50 mol. % and an ethylene selectivity of 90% or more at a temperature from about 350° C. to about 475° C. In some embodiments, the catalyst described, when used in a process for oxidative dehydrogenation of ethane, demonstrates conversion of 50 mol. % and an ethylene selectivity of 90% or more at a temperature of from 390° C. to 450° C. In some embodiments, the catalyst described, when used in a process for oxidative dehydrogenation of ethane, demonstrates conversion of 50 mol. % and an ethylene selectivity of 90% or more at a temperature of from 400° C. to 450° C.

In some embodiments, the catalyst described, when used in a process for oxidative dehydrogenation of ethane, demonstrates conversion of 35 mol. % and an ethylene selectivity of 90% or more at a temperature of at least 400° C.

Furthermore, ODH catalysts are known to show a decrease in activity over time, with the most significant drop occurring shortly after starting usage when the catalyst is still fresh. A catalyst that maintains activity and selectivity over time may prove to be commercially beneficial as the catalyst endures longer before requiring replacement. In some embodiments, the catalyst demonstrates no significant drop in activity or selectivity for at least 110 hours after initial activation. In some embodiments, the catalyst described, when used in a process for oxidative dehydrogenation of ethane, demonstrates an ethane conversion of 50 mol. % and an ethylene selectivity of 90% or more at a temperature of 400° C. or higher for at least 110 hours. In some embodiments, the catalyst described, when used in a process for oxidative dehydrogenation of ethane, demonstrates an ethane conversion of 50 mol. % and an ethylene selectivity of 90% or more at a temperature of from 350° C. to 475° C. for 110 hours. In some embodiments, the catalyst described, when used in a process for oxidative dehydrogenation of ethane, demonstrates an ethane conversion of 50 mol. % and an ethylene selectivity of 90% or more at a temperature of from 400° C. to 450° C. for 110 hours.

Definitions

As used herein, the term "catalyst material" refers to a material that includes a combination of an active catalyst that can promote the oxidative dehydrogenation of ethane to ethylene and a carrier/support material. The catalyst material can be a plurality of particles or a formed catalyst material. Non-limiting examples of formed catalyst materials include extruded catalyst materials, pressed catalyst materials, and cast catalyst materials. Non-limiting examples of pressed and cast catalyst materials includes pellets-such as tablets, ovals, and spherical particles.

As used herein, the term "catalyst" generally refers to the active catalyst portion of a catalyst material. The catalyst is generally processed in further steps to form a catalyst material. The catalyst material may also be processed in further steps to form a final catalyst material.

As used herein, the term "oxidative dehydrogenation" or "ODH" refers to processes that couple the endothermic dehydration of an alkane with the strongly exothermic oxidation of hydrogen as is further described herein.

As used in this disclosure, the phrase "35% conversion temperature" refers to the temperature at which 35 mol. % of ethane in a gas stream is converted to a product other than ethane and is determined using a microreactor unit (MRU) and test conditions described below. Conversion of the feed gas is calculated as a mass flow rate change of ethane in the product compared to the feed ethane mass flow rate using the following formula:

$$CC = \left( \frac{2*X_{C_2H_4} + 2*X_{CH_3COOH} + X_{CO_2} + X_{CO}}{2*X_{C_2H_4} + 2*X_{C_2H_6} + 2*X_{CH_3COOH} + X_{CO_2} + X_{CO}} \right) * 100\%$$

where C is the molar percent of feed gas that has been converted from ethane to another product (i.e., ethane conversion) and X is the molar concentration of the corresponding product in the gaseous effluent exiting the reactor. The ethane conversion is then plotted as a function of temperatures to acquire a linear algebraic equation. The linear equation for ethane conversion is solved to determine the temperature in which the ethane conversion is 35% (i.e., the 35% conversion temperature). The "50% conversion temperature" refers to the temperature at which 50 mol. % of ethane in a gas stream is converted to a product other than ethane and can be determined using the same linear equation.

As used in this disclosure, the phrase "selectivity to ethylene" refers to the percentage on a molar basis of converted or reacted ethane that forms ethylene. An oxidative dehydrogenation catalyst's selectivity to ethylene can be determined using an MRU and test conditions as described below. An oxidative dehydrogenation catalyst's selectivity to ethylene can be determined using to the following equation:

$$S_{C_2H_4} = \left(\frac{2*X_{C_2H_4}}{2*X_{C_2H_4} + 2*X_{CH_3COOH} + X_{CO_2} + X_{CO}}\right)*100\%$$

where $S_{C2H4}$ is the selectivity to ethylene and X is the molar concentration of the corresponding compound in the gaseous effluent exiting the reactor. Notably, the selectivity to ethylene is determined at the indicated conversion temperature, either 35% conversion temperature or 50% conversion temperature. As such, after the 35% conversion temperature is determined, the above equation for selectivity is solved using the corresponding values for $X_{C2H4}$, $X_{CO2}$, and $X_{CO}$ at the 35% conversion temperature.

Oxidative dehydrogenation of ethane may also result in production of various other byproducts including maleic acid, propionic acid, ethanol, acetaldehyde, and their derivatives (e.g. maleic anhydride is produce from hydrolysis of maleic acid). The amounts of these byproducts are insignificant, forming less than 0.1 mol. % of the product, and are therefore not included in the calculations for conversion and selectivity.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

In addition, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

EXAMPLES

Catalysts comprising Mo, V, Te, and Ta were prepared using a staged hydrothermal procedure described below and characterized according to activity (conversion and selectivity), composition (FTIR, XRD, SEM, PSD), and durability (TOS, low oxygen conditions). Selected catalysts were further combined with selected support materials to form catalyst materials and subjected to further characterization.

The general synthesis procedure involved 3 general steps. The first step was the preparation of aqueous solutions of the catalyst precursor salts for each of the elements molybdenum, vanadium, tellurium, and tantalum. The molybdenum and tellurium components were prepared as a combined aqueous preparation to which the vanadium aqueous preparation was added. The tantalum aqueous preparation was then added to form a final aqueous composition. The second step involved hydrothermal baking of the final aqueous composition to form a slurry which was filtered and rinsed to isolate the solid catalyst. The final step included calcination of the solid catalyst. The procedure for synthesis of Catalyst 1.1 comprising the steps as described below served as a baseline procedure for all examples. The modifications to the procedure for additional examples are noted.

Aqueous Preparations

Tantalum oxalate was prepared from tantalum ethoxide via the general description provided in the literature: Grasselli, et. al. (2006). *Topics in Catalysis* 38. 7-16. Aqueous oxalic acid was prepared by dissolving 12.7259 g anhydrous oxalic acid ($C_2O_4H_2$,) in 118 mL of distilled water with the aid of a 65° C. water bath and stirring at 250-450 rpm (enough to create a small vortex), resulting in a clear, colorless solution. The aqueous oxalic acid solution was added all-at-once to 19.10 g $Ta(OEt)_{5(l)}$, immediately producing a white suspension, which was stirred at 65° C. over 2 days to form a clear, colorless, aqueous solution of 0.4 mol Ta/L $H_x[Ta(C_2O_4)_3]_{(aq)}$.

Ammonium heptamolybdate tetrahydrate $(NH_4)_6Mo_7O_{24} \cdot 4H_2O_{(s)}$), 463.89 g, was dissolved in 3500 mL of distilled water to form a clear, colorless solution, and then stirred at 80° C. Telluric acid $(OH)_{6(s)}$, 100.55 g, was added all-at-once to the warm aqueous $(NH_4)_6Mo_7O_{24}$ to form a turbid solution. The pH of the turbid solution was adjusted to 7.5 by slowly adding 191 mL of aqueous $NH_4OH$ (28 wt. % of $NH_3$ in water) to form a clear and colorless solution. The pH of the solution was monitored by a temperature compensation pH meter. The solution was stirred in open air at 80° C. for about approximately 48 hours to evaporate all the water to isolate a clear, colorless solid. The colorless solids obtained were ground and dried overnight to produce a white powder of $(NH_4)_6Mo_6TeO_{24} \cdot 7H_2O_{(s)}$, 59.16 g of which was dissolved in 750 mL of distilled water (set aside 50 mL distilled water for rinsing for all other subsequent mixing and transferring steps) with stirring at 60° C. to create a clear, colorless solution.

Vanadium sulfate ($VOSO_4 \cdot 3.36H_2O$), 39.44 g, was dissolved in 240 mL of distilled water at 60° C. with stirring to create a clear, blue solution. The warm $VOSO_4$ solution was added, dropwise, to the warm aqueous $(NH_4)_6Mo_6TeO_{24}$ solution over approximately 11 minutes to produce a black solution. Immediately after formation of the black MoVTe solution, the entire solution of $H_x[Ta(C_2O_4)_3]_{(aq)}$ was added, dropwise, to produce an olive-green solution, which was allowed to stir in air at 60° C. for 1 hour, during which a fine precipitate formed.

Hydrothermal Baking

The 60° C. olive-green slurry was poured to a glass liner for a 2000 mL PARR autoclave equipped with an overhead stirred reactor head and transferred to an autoclave. The autoclave was closed and the atmosphere inside of the autoclave was evacuated (vacuum) and filled with nitrogen (12 psig from bulk nitrogen line) 10 times. The autoclave was sealed under 12 psig bulk nitrogen and placed into a heating mantel for hydrothermal baking. The heating mantel and autoclave were well insulated and heated to at external control temperature of 175° C. for 48 hours and hydrothermal reaction proceeded at standstill. The external set point temperature was measured via a thermocouple which was located on wall of reactor, underneath the heating mantel. The temperature of the solution, as measured via a wetted process thermocouple through the Hastelloy thermowell was recorded as 166° C. The heat up time from room temp to inside temp of 164° C. was ~4.5 hours.

The reactor pressure and volume were maintained with an apparatus described in U.S. Pat. No. 10,589,258 (B2), assignee NOVA Chemicals International S.A. The apparatus was attached to the reactor head but is a tube-in-shell exchanger (condenser) with cooling water circulating on the outside tubing at ~25° C. (controlled via closed system, cooling bath) and the inside tubing was connected to the reactor (process) to allow venting of excess gaseous pressure via a backpressure regulator. The backpressure regulator setpoint was set to 140 psig and that pressure was recorded on the second day of reaction. The pressure setpoint of 140 psig was determined via referring to the steam table pressure of water heated at 175° C. and a pressure slightly above what is indicated on the steam table was chosen to ensure the liquids reach temperature (i.e., elevated boiling point). Some release of pressure could be observed via a glass water bubbler attached to the outlet side (vent) of the backpressure regulator. Slow bubbling (venting of excess $CO_2$(g) pressure from decomposition of oxalic acid) was observed only on the second day of the 48-hour reaction.

After 48 hours, the reactor was allowed to cool to room temperature and excess carbon dioxide (from oxalic acid decomposition) and nitrogen pressure were vented into a fume hood. The purple slurry when disturbed produced vigorous bubbling of carbon dioxide. The purple solid was filtered through a Buchner funnel with 3× layers of qualitative filter paper to separate the blue mother liquor from the dark purple (almost black) solids. The solids were rinsed with approximately five portions of 400 mL of distilled water until the filtrate no longer had any visible blue color after passing through the solids. The solids were then dried in an oven at 90° C. overnight before crushing into small particles using a mortar/pestle.

Calcination

A portion of the of the crushed recovered product was loaded in a quartz boat and the boat was placed into quartz tube for calcination. The quartz tube was purged with bulk nitrogen (<10 ppm oxygen) at a flow rate of 30 sccm, with the outlet side of the tube being vented through a silicone oil bubbler to help maintain the tube under an anaerobic atmosphere. The tube atmosphere was purged for 6 hours with bulk nitrogen (<10 ppm oxygen) and then the inlet bulk nitrogen was redirected through an oxygen trap (LabClear OxiClear™ gas purifier) to purge the tube with purified nitrogen (<1 ppm oxygen) for an additional 12 hours. The calcination proceeded under 30 sccm purified nitrogen flow with the following heating conditions: RT (~20° C.) to 600° C. in 6.25 hours (1.6° C./min), held at 600° C. for 2 hours, and left to cool naturally.

The additional catalyst examples were prepared by varying the amounts of starting materials and with the following modifications to the general procedure:

Catalyst 1.2: Increased the amount of tantalum ethoxide to 23.1 g and during hydrothermal baking the external control temperature was set to 185° C. and the slurry was subjected to stirring at 150 rpm.

Catalyst 1.3: During hydrothermal baking the slurry was subjected to stirring at 20 rpm.

Catalyst 1.4: Tantalum oxalate was commercially sourced as opposed to preparation by digesting tantalum ethoxide with oxalic acid.

Catalyst 1.5: Tantalum oxalate was commercially sourced, and the amount was reduced by a factor of 1.94 compared to catalyst 1.1.

Catalyst 1.6: Same procedure used for Catalyst 1.5.

Catalyst 1.7: The $(NH_4)_6Mo_6TeO_{24} \cdot 7H_2O_{(s)}$ was produced in situ in aqueous solution, rather than being isolated as a solid, using a two-step pH adjustment with the first adjustment to pH~7.5 with $NH_4OH_{(aq)}$ and then second adjustment to pH~5 with $H_2SO_{4(aq)}$.

Catalyst 1.8: Followed the same procedure as Catalysts 1.5 and 1.6 but with in situ preparation of $(NH_4)_6Mo_6TeO_{24} \cdot 7H_2O_{(s)}$ using a single pH adjustment to ~5.0 using $NH_4OH_{(aq)}$.

Catalyst 1.9: Followed the same procedure as Catalyst 1.1 but at an approximately 5-fold larger scale.

Comparative example Catalyst 2.1 was prepared by following the procedure outlined for Example 1 in US20100222623. Specifically, 20.9995 g of $(NH_4)_6Mo_7O_{24} \cdot 4H_2O_{(s)}$ was dissolved in 150 mL of distilled water at 80° C. with the aid of stirring. $Te(OH)_{6(s)}$, 7.64 g, was dissolved in 85 mL of distilled water at 80° C. with the aid of stirring. The solution of $Te(OH)_{6(aq)}$ was added all-at-once to the solution of $(NH_4)_6Mo_7O_{24(aq)}$ at 80° C. to produce a clear and colorless solution and stirred for 15 minutes at 80° C. To the 80° C. MoTe-solution was added all-at-once 4.5940 g of $NH_4VO_{3(s)}$ to instantly produce a vibrant orange solution, which was stirred at 80° C. for 5 minutes, during which some trace amounts of solid precipitate formed. The stirred, orange mixture was then allowed to cool to room temperature over 45 minutes. To the room temperature orange mixture was added 11.742 mmol of clear-and-colorless aqueous tantalum oxalate dropwise over 20 minutes, which resulted in a clear, orange solution. The aqueous tantalum oxalate used was prepared in the same fashion as outlined in Example 1, e.g. from aqueous oxalic acid digestion of tantalum oxide precipitated from $Ta(OEt)_{5(l)}$.

The resulting orange mixture was evaporated via 650 mm Hg vacuum with the aid of heating at 50° C. (via a heated water bath) and stirred at 500 rpm. During the water removal, orange solids were observed roughly halfway through the evaporation. After all visible water was removed, a light orange solid was obtained, which was dried in an oven at 120° C. for 4 hours to produce a dark orange solid, which was via a mortar-and-pestle and weighed at 34.8748 g.

The entirety of the 34.8748 g of ground dark orange solid was loaded into a quartz boat for calcination in a quartz tube, reactor furnace. Before calcination, the quartz tube containing the to-be calcined solids was purged with bulk nitrogen (<10 ppm oxygen) at a flow rate of 30 sccm, with the outlet side of the tube being vented through a silicone oil bubbler to help maintain the tube under an anaerobic atmosphere. The tube atmosphere was purged for 6 hours with bulk nitrogen (<10 ppm oxygen) and then the inlet bulk nitrogen was redirected through an oxygen trap (LabClear Oxi-Clear™ gas purifier) to purge the tube with purified nitrogen (<1 ppm oxygen) for an additional 12 hours. The calcination proceeded under 30 sccm purified nitrogen flow with the following heating conditions: RT to 600° C. in 1 hour (approx. 10° C./min), held at 600° C. for 2 hours, and left to cool naturally.

After calcination, the resulting black, hard, sintered powder, Catalyst 2.1, which was weighed at 26.8901 g, a weight yield of 77.1%. It was noted that the outlet of the quartz tube was significantly coated with grey, sublimed deposits, considerably more-so than that was observed for any of the inventive examples.

Catalyst Materials

Catalyst materials which comprise a catalyst and a carrier/support material were prepared using catalysts 1.1, 1.6, and for comparison catalyst 2.1. Activity assessments, along with physical characterizations, were performed to determine which supports or carriers were suitable or compatible for use in a catalyst material. Compatibility was determined by catalysis testing of catalyst materials on an MRU reactor and observing an initial (within the first 8 hours of testing) high ethylene selectivity, e.g., >89 mol. % selectivity for ethylene at approx. 50 mol. % ethane conversion. Preparation of catalyst materials was as follows.

Catalyst material 1.1 was produced by mixing catalyst 1.6 with synthetic amorphous silica to target a combined weight product of 40 wt. % catalyst 1.6 and 60 wt. % support. The synthetic amorphous silica applied in this example was obtained from PQ Corporation, product identifier CS6846; PD-10042, and classified as precipitated synthetic (precipitation from alkali silicate solutions) and categorized under CAS-No. 112926-00-8. Catalyst 1.6, 4.0375 g, and precipitated synthetic silica, 6.0493 g, were suspended together in 35 mL of distilled water to form a slurry, which was heated to 100° C. and stirred at 80 rpm via a motor driven, overhead Teflon agitator. Agitation and heating at 100° C. was continued until enough water was evaporated to form a thick paste (consistency of modeling clay) and then dried overnight in a 90° C. oven. After oven drying, the entirety of the remaining material, 9.6999 g, was loaded in a quartz boat, which was inserted into a quartz tube of a split tube furnace. The tube was sealed and purged with non-purified nitrogen (<10 ppm oxygen concertation) atmosphere at 14 sccm flow at room temperature overnight. 2 hours before starting furnace heating, the purge was switched to purified nitrogen (e.g. non-purified nitrogen was redirected through an oxygen trap, LabClear OxiClear™ gas purifier, to produce <1 ppm oxygen containing nitrogen). The purified nitrogen flow was reduced to 5 sccm and the furnace was heated to 500° C. at the rate of 1.6° C./min, held for 2 hours at 500° C. and then cooled down (heater off). The catalyst was removed and weighed (9.2891 g-95.8% mass yield). A second calcination, where the sample was transferred to a 50 mL beaker and calcined in air at 250° C. for 2 hours, with a 2 hour ramp rate for both heating and cooling, was performed to produce catalyst material 1.1.

Specifically, produced by mixing catalyst 1.6 with synthetic amorphous silica to target a combined weight product of 40 wt. % catalyst 1.6 and 60 wt. % silica. The synthetic amorphous silica applied in this example was obtained from Sigma-Aldrich Corporation, product number S5130, and classified as fumed synthetic (produced by flame hydrolysis of silicon tetrachloride or analog) and categorized under CAS-No. 112945-52-5. 1.6. Fumed synthetic silica, 6.0015 g, was mixed with 50 mL of distilled water to form a silica gel which was transferred to a 50 mL beaker containing 4.0002 g of catalyst 1.6. The contents of the beaker were mixed with a spatula to generate a slurry before heating at 100° C. in an oil bath and stirred at 80 rpm via a motor driven, overhead Teflon agitator. The beaker was agitated and heated at 100° C. for approx. 3.5 hours, until enough water was evaporated to form a thick paste (consistency of modeling clay) and then removed from the oil bath. The paste containing beaker was placed in a 90° C. oven and dried overnight at standstill. After oven drying, 9.6906 g of material was recovered, the entirety of the Catalyst Material was ground with a mortar/pestle and loaded in a quartz boat, which was inserted into a quartz tube of a split tube furnace. The tube was sealed and purged with non-purified nitrogen (<10 ppm oxygen concertation) atmosphere at 14 sccm flow at room temperature overnight. 2 hours before starting furnace heating, the purge was switched to purified nitrogen (e.g. non-purified nitrogen was redirected through an oxygen trap, LabClear OxiClear™ gas purifier, to produce <1 ppm oxygen containing nitrogen). The purified nitrogen flow was reduced to 5 sccm and then the furnace was heated to 500° C. at the rate of 1.6° C./min, held for 2 hours at 500° C. and then cooled down (heater off). The catalyst was removed and weighed. The weight of catalyst material 1.2 after calcining was 9.4840 g (96.2% mass yield). The sample (9.3224 g) was transferred to a 50 mL beaker and calcined in air at 250° C. for 2 hours, with a 2 hour ramp rate for both heating and cooling. After the second calcination, 9.4840 g of catalyst material 1.2 was recovered.

Catalyst material 1.3 was produced by mixing catalyst 1.6 with aluminum silicate to target a combined weight product of 40 wt. % catalyst 1.6 and 60 wt. % aluminum silicate. The aluminum silicate applied in this example was obtained from Sigma-Aldrich, product number 343358, and assigned the product name: Silica-alumina catalyst support, grade 135.

The Aluminum silicate categorized as aluminum salt of silicic acid based on its assignment of CAS-No. 1335-30-4. Catalyst material 1.3 was prepared following the procedure used for catalyst material 1.1, starting with 4.0021 g of catalyst 1.6 and 5.9995 g of Sigma-Aldrich silica-alumina catalyst support, grade 135. After 500° C. nitrogen calcination, the weight was 9.8475 g (99.9% mass yield). After the 250° C. air calcination, the mass of catalyst material 1.3 recovered was 9.8451 g (100.01% mass yield).

Catalyst material 1.4 was produced by mixing catalyst 1.6 with α-alumina to target a combined weight product of 40 wt. % Catalyst Composition and 60 wt. % support. The α-alumina applied in this example was obtained from Saint-Gobain, product name: DENSTONE® 99. DENSTONE 99 is >99 wt. % aluminum oxides, CAS-No. 1344-28-1. Before application, the DENSTONE 99 α-alumina was ground and passed through a #60 sieve to ensure particle size<250 μm. Catalyst material 1.4 was prepared following the described previously for catalyst material 1.1, starting with 4.0013 g of catalyst 1.6 and 5.9998 g of ground α-alumina. After 500° C. nitrogen calcination, the weight was 9.9876 g (99.7% mass yield). After the 250° C. air calcination, the mass of catalyst material 1.4 recovered was 9.8959 g (100.01% mass yield).

Catalyst material 1.5 was produced by mixing catalyst 1.6 with anatase titania to target a combined weight product of 40 wt. % catalyst 1 and 60 wt. % anatase titania. The anatase titania applied in this example was Sigma Aldrich product number 232033, CAS-No. 1317-70-0. Catalyst material 1.5 was prepared according following the procedure, described previously for catalyst material 1.1, starting with 4.0004 g of catalyst 1.6 and 5.9999 g of anatase titania. After 500° C. nitrogen calcination, the weight of catalyst material 1.5 was 9.6920 g (99.7% mass yield). After the 250° C. air calcination, the mass of catalyst material 1.5 recovered was 9.6605 g (99.7% mass yield).

The following catalyst supports (carriers) were determined to be incompatible with a catalyst once mixed and were deemed unsuitable for use in a catalyst material. Incompatibility was determined by catalysis testing of Catalyst Materials on a MRU reactor and observing an appreciable loss in ethylene selectivity, e.g., <90 mol. % selectivity for ethylene at approx. 50 mol. % ethane conversion. In some cases, if the resulting catalyst material was very inactive, then the catalyst composition was also considered incompatible with the support.

Catalyst material 2.1 was produced by mixing catalyst 1.6 with silicon carbide to target a combined weight product of 40 wt. % catalyst 1.6 and 60 wt. % silicon carbide. The silicon carbide applied in this example was obtained from Saint-Gobain, product code: SC55167, 13 wt. % $SiO_2$ and the balance SiC (CAS-No. 409-21-2). Before application, the silicon carbide was ground and passed through a #60 sieve to ensure particle size<250 µm. Catalyst material 2.1 was prepared following the procedure described previously for catalyst material 1.1, starting with 4.0017 g of catalyst 1.6 and 6.0005 g of ground silicon carbide. After 500° C. nitrogen calcination, the weight was 9.8806 g (99.5% mass yield). After the 250° C. air calcination, the mass of catalyst material 2.1 recovered was 11.9546 g (121.0% mass yield.)

Catalyst material 2.2 was produced by mixing catalyst 1.6 with colloidal alumina to target a combined weight product of 40 wt. % catalyst 1.6 and 60 wt. % support. The colloidal alumina applied in this example was Alfa Aesar, Cat No. 12733, which contained 20 wt. % $Al_2O_3$ dispersed in water. Catalyst material 2.2 was prepared following the procedure described previously for catalyst material 1.1, starting with 4.0418 g of catalyst 1.6 and 30.0648 g of 20 wt. % $Al_2O_3$.

Catalyst material 2.3 was produced by mixing catalyst 1.1 with boehmite aluminum oxide hydroxide to target a combined weight product of 40 wt. % catalyst 1.1 and 60 wt. % boehmite aluminum. The boehmite aluminum oxide hydroxide applied in this example was obtained from Honeywell UOP, product name Versal V-250 (No. 86251), which is described as a low density pseudoboehmite alumina (wt. %<95%; CAS-No. 1344-28-1). For synthesis, to a 50 mL beaker was charged 4.0263 g of catalyst 1.1 and 6.0622 g of boehmite aluminum oxide hydroxide, forming a slurry with the addition of sufficient amounts of distilled water to create a suspension. The beaker containing slurry was placed in an oil bath, which was heated to 100° C. and stirred at 85 rpm via a motor driven, overhead Teflon agitator. The beaker was agitated and heated at 100° C. until enough water was evaporated (approx. 3 hours) to form a thick paste (consistency of modeling clay) and then removed from the oil bath. The paste containing beaker was placed in a 90° C. oven and dried overnight at standstill. After oven drying the recovered material was loaded in a quartz boat, which was inserted into a muffle furnace and calcined in air by heating up to 350° C. in air over 4 hours, holding the temperature at 350° C. overnight and then cooling down naturally (heater off). The recovered solids were used as catalyst material 2.3.

Catalyst material 2.4 was produced by mixing catalyst 1.6 with calcium titanate to target a combined weight product of 40 wt. % catalyst 1.6 and 60 wt. % calcium titanate. The calcium titanate applied in this example was Goodfellow Corporation product code: CA546, which is classified as 80-100 wt. % calcium titanium oxide ($CaTiO_3$) and categorized under CAS-No. 12049-50-2. Catalyst material 2.4 was prepared following the procedure described previously for catalyst material 1.1, starting with 3.9986 g of catalyst 1.6 and 6.0013 g of calcium titanate powder. After 500° C. nitrogen calcination, the weight was 9.7932 g (99.2% mass yield). After the 250° C. air calcination, the mass of catalyst material 2.4 recovered was 9.7813 g (100.02% mass yield).

Catalyst material 2.5 was produced by mixing catalyst 1.6 with zirconia powder to target a combined weight product of 40 wt. % catalyst 1.6 and 60 wt. % support. The zirconium (IV) oxide applied in this example was Sigma Aldrich product number 204994, CAS-No. 1314-23-4. Catalyst material 2.5 was prepared following the procedure described previously for catalyst material 1.1, starting with 4.0001 g of catalyst 1.6 and 6.0015 g of zirconia. After 500° C. nitrogen calcination, the weight was 9.6723 g (99.3% mass yield). After the 250° C. air calcination, the mass of catalyst material 2.5 recovered was 9.6725 g (101.1% mass yield).

Catalyst material 2.6 was produced by mixing catalyst 1.6 with colloidal zirconia to target a combined weight product of 40 wt. % catalyst 1.6 and 60 wt. % colloidal zirconia. The colloidal zirconia applied in this example was Alfa Aesar, Cat No. 40124, which contained 20 wt. % $ZrO_2$ dispersed in water. Catalyst material 2.6 was prepared following the procedure previously described for catalyst material 1.1, starting with 4.0371 g of catalyst 1.6 and 30.0044 g of 20 wt. % $ZrO_2$ colloidally dispersed in water.

Performance

The prepared catalysts and catalyst materials were subjected to testing in relation to their physical properties and ability to convert ethane into ethylene. Performance of the catalyst was assessed for 35% and 50% conversion temperatures, and corresponding selectivities to ethylene. The catalysts and catalyst materials were further tested for robustness. That is, they were tested to assess effects on conversion and selectivity over longer time periods as many oxidative dehydrogenation catalysts have been shown to have reduced activity, selectivity, or both over time. Finally, the catalysts, and catalyst materials, were assessed for resilience to low residual oxygen levels and selectivity to acetic acid.

MRU

The ability of catalysts and catalyst materials described herein to participate in the oxidative dehydrogenation of ethane were tested in a microreactor unit (MRU) 100, shown in cross-section in FIG. 1. MRU 100 consists of a vertically oriented reactor tube 1 formed from stainless-steel SWAGELOK® tubing having an outer diameter of 0.5 inches, an inner diameter of 0.4 inches, and a length of 13.4 inches, surrounded by a two-zone electrical heater 2 or tube furnace and connected to tubing above and below via SWAGELOK connections 6. A catalyst bed 3 (gray shading) containing the catalyst, or catalyst material, situated at or near the middle of the reactor tube (along the length) was secured in place by packing 4 comprising glass wool bordering the upper (4a) and lower (4b) boundaries of the catalyst bed (hatched shading). A 6-point WIKA Instruments Ltd. K-type thermocouple 5 having an outer diameter of 0.125 inches inserted through the center of and along the length of the reactor tube 1 was used to measure the temperature within the catalyst bed. The temperature input from thermocouple 5 was used to control the power output to the electrical heater 2 in order to control the temperature inside the reactor. The 6-points, indicated by hollow circles, are spread along the length of reactor tube 1, with points 3 and 4 situated within the catalyst bed 3. A room temperature stainless steel condenser was located downstream of the reactor to collect water/acetic acid condensates. The gas product flow was allowed to either vent or was directed to a gas chromatography (GC; Agilent 6890N Gas Chromatograph, Using Chrom Perfect—Analysis, Version 6.1.10 for data evaluation) via a sampling loop (not shown).

To prepare catalyst and catalyst materials for testing on the MRU, the catalyst or catalyst material was loaded into a 1-inch round die and pressed with 12 metric tons of compression force and held under this pressure for at least 10 seconds. The resulting puck of pressed catalyst or catalyst material was then crushed into small pieces using a mortar and pestle. The crushed catalyst or catalyst material was sieved and a particle sizes between 425 μm and 1000 μm were collected to be loaded for testing on the MRU.

For standard catalyst testing, 2.00 g of sieved catalyst from crushed pressed catalyst, with particle size ranging from 425 μm and 1000 μm, was physically mixed with quartz sand such that the mixture produced a catalyst bed total volume of 6 ml. Once the catalyst bed was loaded into the reactor and connected to the MRU equipment, a pre-mixed feed gas comprising 20 mol. % ethane, 10 mol. % oxygen, and 70 mol. % nitrogen (ethane-to-oxygen mol ratio of 1/0.5) was passed through reactor tube 1 from upper tubing 8 (direction indicated by hollow arrow), with effluent gas leaving through lower tubing 9. The pre-mixed feed was prepared using gas blending equipment and involved calibrated mass flow controllers (not shown). An outlet pressure of 20 psig was maintained using a back-pressure regulator (not shown). The flow of the pre-mixed feed gas was controlled to 152 standard cubic cm (sccm) in order to achieve a constant weight hourly space velocity (WHSV) of 5.46 $h^{-1}$ for all catalyst testing experiments, where WHSV is defined as mass flow of feed gas to the reactor divided by the weight of the catalyst in the catalyst bed. The gas exiting the reactor was analyzed by GC (Agilent 6890N Gas Chromatograph, Using Chrom Perfect—Analysis, Version 6.1.10 for data evaluation) to determine the percent of various hydrocarbons (e.g., ethane and ethylene) and optionally other gases such as $O_2$, $CO_2$, and CO and acetylene, with the results being used to calculate conversion and selectivity as defined above. Temperature was monitored in real-time at all 6 points, with the average of points 3 and 4 (which are within the catalyst bed) providing the temperatures used for plotting conversion versus temperature.

Several catalysts were subjected to a modified MRU setup and operating conditions. Specifically, the length of reactor tube 1 was 15 inches and catalyst loading included from 2.00 to 4.00 g of crushed pressed catalyst in a catalyst bed volume of 6 ml. Further, the pre-mixed feed gas entering reactor tube 1 was 35 mol. % ethane, 17.5 mol. % oxygen, and 47.5 mol. % nitrogen (ethane-to-oxygen mol ratio of 1/0.5), with the reactor operating at close to ambient reactor outlet pressure, with internal reactor pressures stemming from dP due to reactor bed loading registering less than 3 psig. The flow of the pre-mixed feed gas was controlled between 76 to 152 standard cubic cm (sccm) depending on weight loading in order to achieve a constant weight hourly space velocity (WHSV) of 2.79 $h^{-1}$. The modified method produced was associated with higher temperatures for conversion, which is not surprising considering the pressure difference when compared to the standard method described above. Limitations on conversion and selectivity described herein are intended to represent limitations measured using the standardized methodology using a 15 inch reactor tube with 0.4 inch internal diameter, under conditions where the feed gas comprises 20 mol. % ethane, 10 mol. % oxygen, and 70 mol. % nitrogen, the WHSV is held at 5.46 $h^{-1}$, and the pressure is held at 20 psig.

MRU Catalyst Testing data for Catalysts 1.1-1.9, and 2.1 where the temperature was increased incrementally to determine the catalyst performance is shown in Table 1 below. At each temperature interval, GC data was collected on the product gas composition. The raw GC data when then used to produce linear algebraic expression to produce the below tabulated results for ethane conversion (35 and 50 mol. %) and the corresponding ethylene selectivity (mol. %).

The data in Table 1 indicates that the conversion temperatures for the majority of the catalysts are significantly lower than the comparative example 2.1, which demonstrated poor activity as conversion had not reached 35 mol. % or 50 mol. % before the temperature of the reactor reached 500° C. With the exception of catalysts 1.2 and 1.7, the examples all display ethylene selectivities greater than 90%, even at the 50 mol. % conversion temperature. Furthermore, the results for catalyst 1.9 demonstrate that scaling up the synthesis to provide larger quantities has no deleterious effects on the performance, and in fact catalyst 1.9 actually shows better performance than catalyst 1.1, with lower conversion temperatures and similar ethylene selectivity. Note that catalysts 1.1 and 1.5 were assessed using both the standard MRU method and the modified method, with no effect on selectivity but the conversion temperatures were higher for the modified method by from 14° C. to 39° C. Asterisks indicate samples that were only assessed using the modified method.

TABLE 1

| Catalyst | 35% Conversion Temperature (° C.) | Selectivity to Ethylene at 35% Conversion Temperature (%) | 50% Conversion Temperature (° C.) | Selectivity to Ethylene at 50% Conversion Temperature (%) |
|---|---|---|---|---|
| 1.1 | 413 | 93 | 443 | 91 |
| 1.2* | >>500 | — | >>500 | — |
| 1.3* | 412 | 95 | 441 | 93 |
| 1.4* | 457 | 93 | 497 | 91 |
| 1.5 | 419 | 93 | 447 | 91 |
| 1.6 | 411 | 95 | 438 | 93 |
| 1.7* | 453 | 83 | 491 | 79 |
| 1.8 | 431 | 95 | 464 | 94 |
| 1.9 | 388 | 95 | 413 | 93 |
| 2.1* | >>500 | — | >>500 | — |

Catalysts 1.1 and 1.6 were selected for assessment of suitable supports. Suitable or compatible supports assessed by determining the effect of combining the catalyst with the support on selectivity and conversion. MRU testing of catalyst materials followed the procedure for standard testing described above. Specifically, 4.00-5.00 g of pressed catalyst material, with particle size ranging from 425 μm and 1000 μm, was physically mixed with quartz sand such that the mixture produced a catalyst bed total volume of 6-8 mL. In cases where the density of the catalyst material was too low and 5 g of catalyst material reached the volume of 6 mL, no sand was added. In cases where the density of the catalyst material was too low and 5 g of catalyst exceeded 6 mL, a maximum volume of 8 mL of catalyst was loaded, and the flow was adjusted to maintain the WHSV specification of 5.47 $h^{-1}$. Since all catalyst materials were prepared with 40 wt. % catalyst, the weight loading of catalyst in the MRU testing equipment was in the range of 1.60-2.00 g. The flow of the pre-mixed feed gas was controlled between 126 to 152 standard cubic cm (sccm) depending on weight loading, in order to achieve a constant weight hourly space velocity (WHSV) of 5.46 h$^{-1}$ for all catalyst materials testing.

It should be apparent to the person skilled in the art that using variable catalyst amounts and catalyst bed total volume as described will not have a significant impact on measured conversion and selectivity, provided that the measurements are obtained using identical reactor dimensions, feed compositions, operating pressure, and a WHSV of 5.47 h$^{-1}$, as described above. The limits on conversion and selectivity as described and claimed herein are measured under the conditions described.

The data in Table 2, which was collected on an MRU using standard catalyst testing described above, indicates that the support materials comprising precipitated silica, fumed silica, aluminum silicate, α-alumina, anatase titania, and zirconia powder provide the best results, with conversion and selectivity holding below 431° C. and above 87%, respectively. In contrast, the support materials comprising silicon carbide, colloidal alumina, boehmite aluminum, calcium titanate, and colloidal zirconia do not appear to be compatible due to large decreases in selectivity.

TABLE 2

| Catalyst Material | Support/Carrier | 35% Conversion Temperature (° C.) | Selectivity to Ethylene at 35% Conversion Temperature (%) | 50% Conversion Temperature (° C.) | Selectivity to Ethylene at 50% Conversion Temperature (%) |
|---|---|---|---|---|---|
| 1.1 | Precipitated silica | 431 | 90 | 454 | 87 |
| 1.2 | Fumed silica | 413 | 91 | 446 | 88 |
| 1.3 | Aluminum silicate | 427 | 93 | 462 | 91 |
| 1.4 | α-alumina | 422 | 94 | 457 | 92 |
| 1.5 | Anatase titania | 417 | 92 | 459 | 89 |
| 2.1 | Silicon carbide | 426 | 87 | 466 | 79 |
| 2.2 | Colloidal alumina | 446 | 61 | >500 | <60 |
| 2.3 | Boehmite aluminum | 419 | 82 | 455 | 75 |
| 2.4 | Calcium titanate | 442 | 86 | 476 | 82 |
| 2.5 | Zirconia powder | 403 | 91 | 441 | 87 |
| 2.6 | Colloidal zirconia | 453 | 47 | >500 | <40 |

Robustness

It is common for a fresh catalyst to show robust activity which declines over time. Without wishing to be bound by theory, this effect may be due to elements within the catalyst undergoing sublimation, resulting in a change in the structure and composition. Catalysts with a more stable structure and phase composition may maintain high conversion and selectivity over time and are therefore more conducive for use in a commercial process as they can endure longer before requiring replacement.

Robustness testing was performed on the catalysts and catalyst materials in an MRU, using standard testing conditions described above with respect to catalyst loading, feed gas composition, pressure, and WHSV. Effluent gas monitoring by gas chromatography (GC) was used to adjust temperature to provide for predetermined criteria, either the 50% conversion temperature or the residual oxygen levels (mol. %). Determinations of the 50% conversion temperature for each of the catalyst materials tested was used as an estimate for the temperature required to provide for 50% conversion. The inherent variability (~1-3 degrees) meant that conversions at set temperature did not always fall at 50%. For robustness testing of catalysts, the temperature was set to provide for 50% conversion. If conversion steadily declined and plateaued the temperature was then adjusted to provide for 50% conversion. Runs progressed for up to 48 hours (and up to 144 hours).

For robustness testing of catalyst materials, the temperature was set and maintained throughout the time on stream. Runs progressed for up to 48 hours (and up to 144 hours) but were stopped when conversion or selectivity dropped to unacceptable levels (for example catalyst material 2.1).

Figure 2:
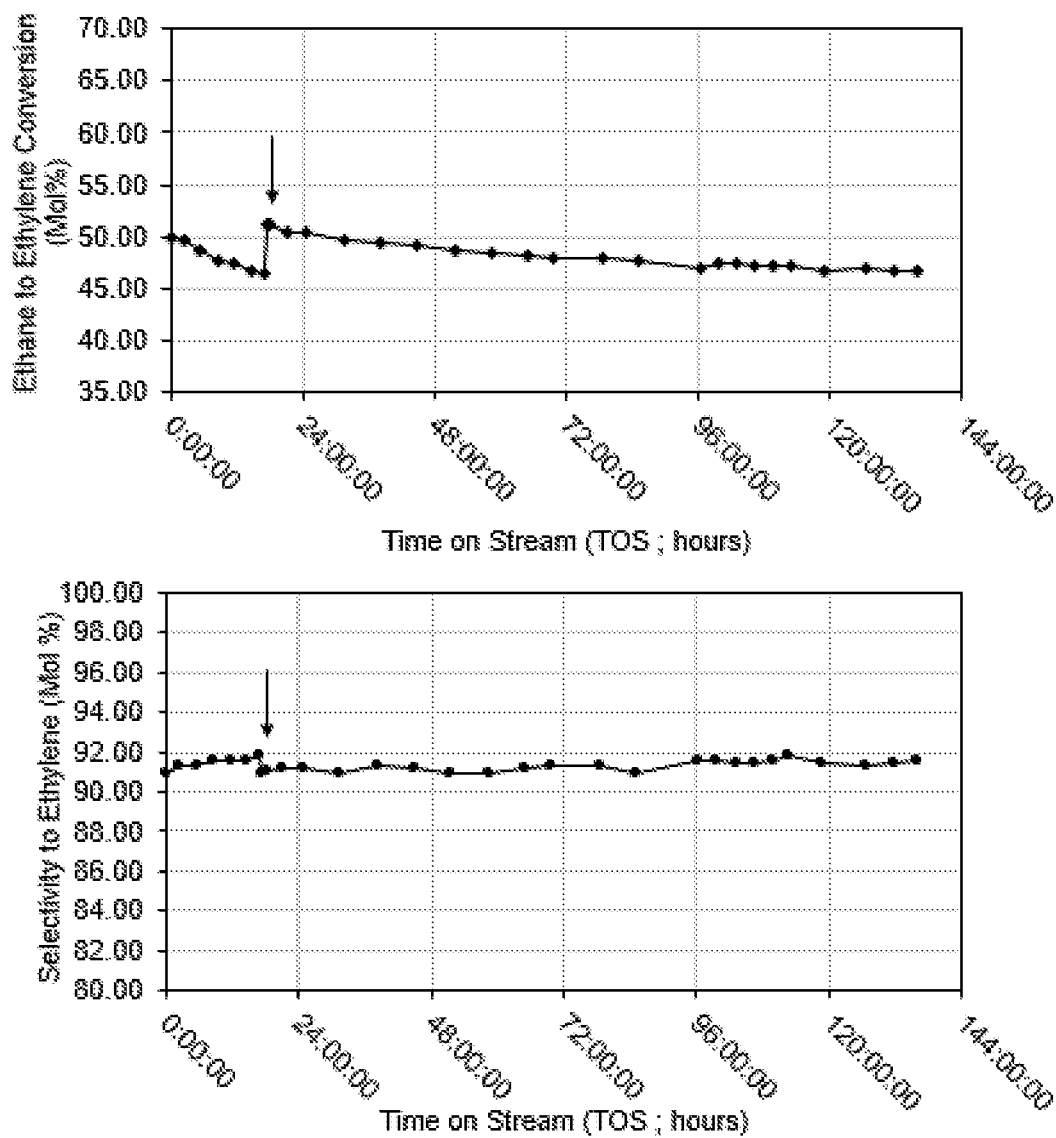
FIG. 2 shows plots of conversion and selectivity as a function of time for catalyst 1.1 at an initial operating temperature of 440° C., followed by an increase in operating temperature of 448° C. after ~15 hours to provide for 50% conversion.

FIG. 2 shows the effect of long-term testing for catalyst 1.1, the results achieved with a time on stream (TOS) of ~144 hours. Catalyst 1.1 was previously determined to have a 50% conversion temperature of ~443° C. (Table 1). A similar temperature of 440° C. was then used for calibration based on the previous determination. The catalyst showed a minor decrease in conversion (upper panel) during the calibration period (~15 hours), but no significant change in selectivity (lower panel). The temperature was then increased (indicated by arrow) to 448° C. to provide for a 50% conversion and held for the duration. The catalyst again showed a minor decrease in conversion over time but stabilized as the curve flattened out. The selectivity essentially stayed constant throughout. The WHSV was held constant throughout at 5.47 h$^{-1}$. These results indicate that catalyst 1.1 is stable and capable of maintaining activity and selectivity over time.

Figure 3:
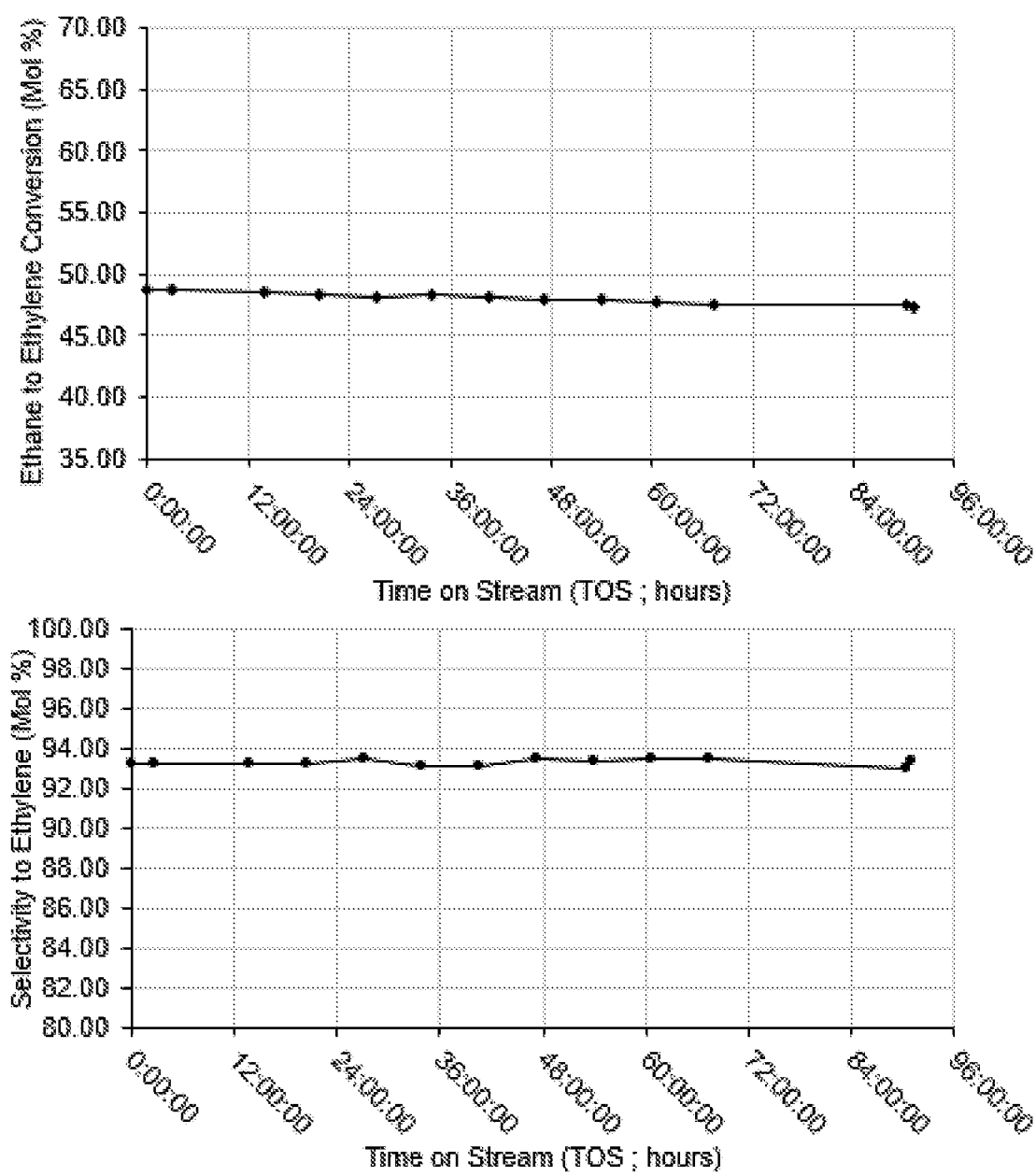
FIG. 3 shows plots of conversion and selectivity as a function of time for catalyst 1.6 at an operating temperature of 442° C., which was maintained for the duration.

FIG. 3 shows the effect of long-term testing for catalyst 1.6, the results achieved with a time on stream (TOS) of ~96 hours, where the temperature was maintained at 442° C. throughout. The catalyst showed no appreciable change in conversion (upper panel) or selectivity (lower panel). These results indicate that catalyst 1.6 is stable and capable of maintaining activity and selectivity over time at a temperature of 442° C.

Figure 4:
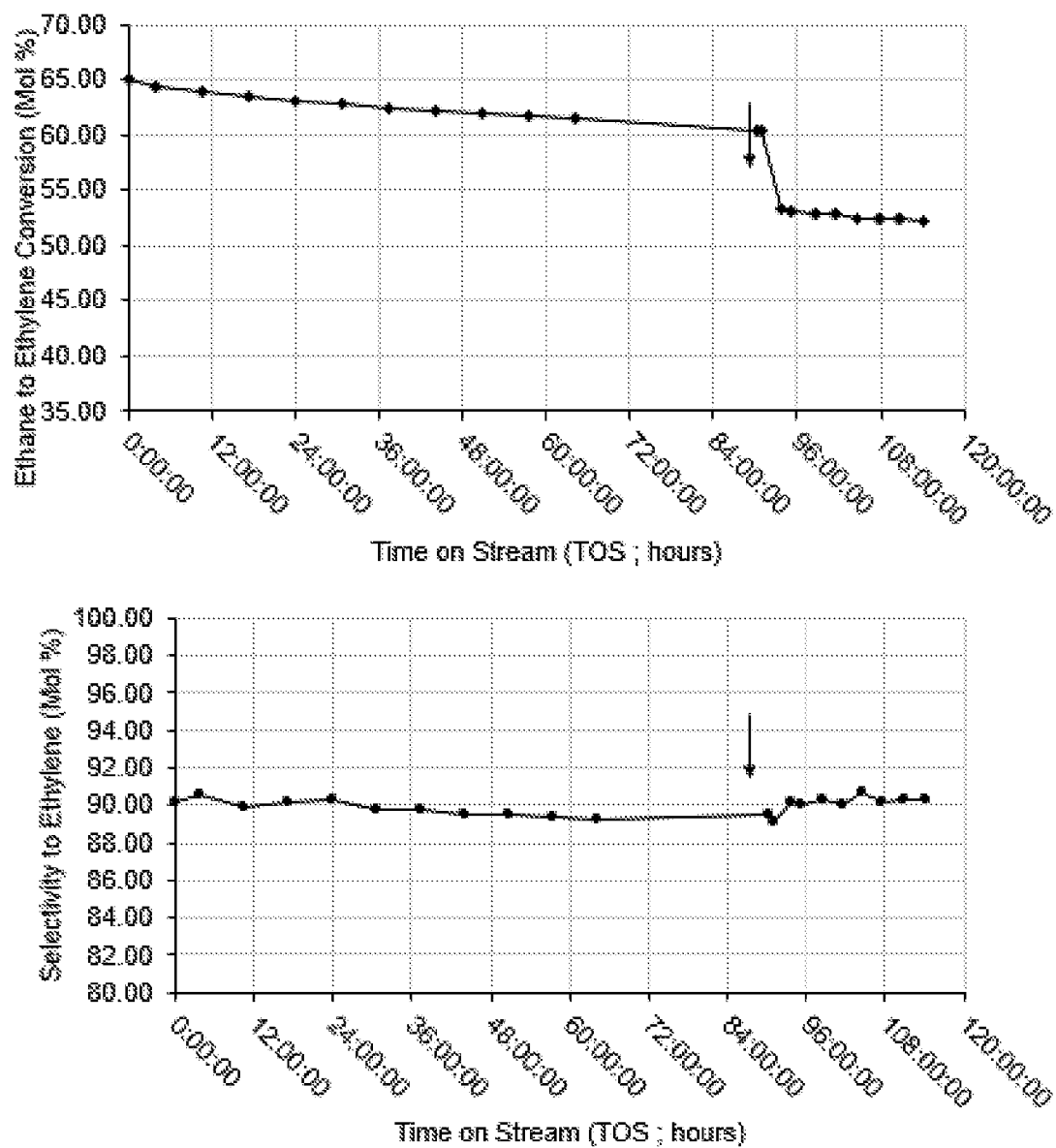
FIG. 4 shows a plot of conversion and selectivity as a function of time for catalyst 1.6 starting with an operating temperature of 470° C., providing for a residual oxygen content of 0.27 mol. %. Operating temperature was reduced to 455° C. after ~87 hours to provide for 50% conversion.

FIG. 4 shows the effect of long-term testing for catalyst 1.6 under low residual oxygen, the results achieved with a time on stream (TOS) of ~120 hours. The starting temperature for robustness testing of catalyst 1.6 was set at a temperature (470° C.) to provide a residual oxygen content in the effluent stream of ~0.27 mol. %. Conversion (upper panel) decreased slowly over ~87 hours before the temperature was changed to 455° C. (indicated by the arrow) to provide a conversion rate of ~50%. Selectivity (lower panel) remained essentially constant throughout, with a slight increase after the temperature was dropped to 455° C. The results demonstrate that catalyst 1.6 is stable and capable of maintaining activity and selectivity over time. Furthermore, catalyst 1.6 appears to be resilient at low residual oxygen content. This is important because many known catalysts have been shown to become irreversibly deactivated at low oxygen levels.

Similar results were seen with catalyst 1.5 (not shown), where conversion decreased slightly over 120 hours while selectivity showed no appreciable change, hovering at ~91%. The comparable catalyst, catalyst 2.1, was not subjected to robustness testing as conversion did not reach 35%, even at temperatures greater than 500° C. (Table 1).

Figure 5:
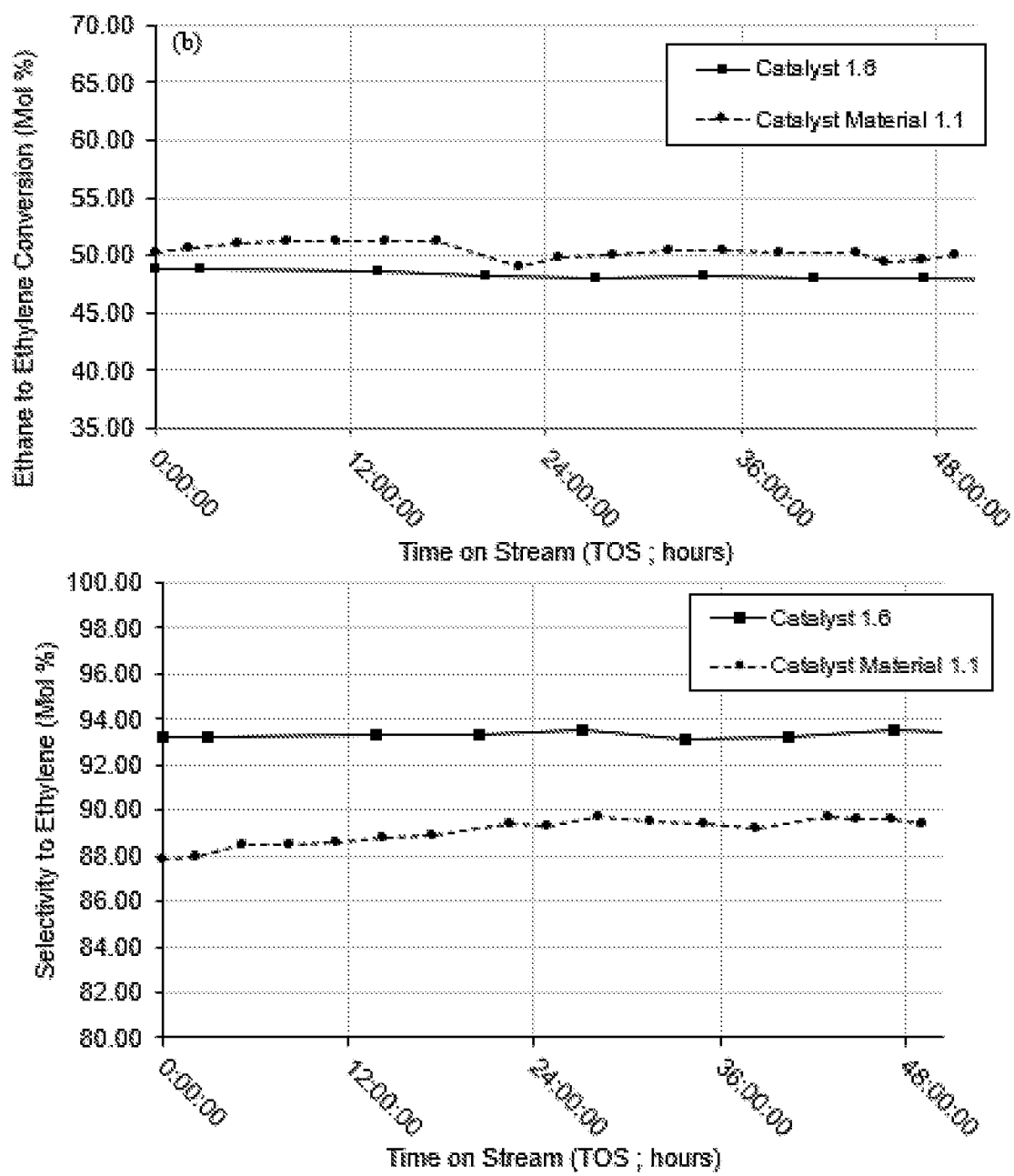
FIG. 5 shows plots of conversion and selectivity as a function of time for catalyst material 1.1 (including catalyst 1.6 for comparison) while maintaining the operating temperature at 455° C. to provide for 50% conversion.

To demonstrate the effect of combining the catalyst with a support on conversion and selectivity, robustness testing was performed on catalyst materials formed from catalyst 1.6. FIG. 5 shows the effect of long-term testing for catalyst material 1.1, with results for catalyst 1.6 included for comparison, with a time on stream (TOS) of ~48 hours. The starting temperature for robustness testing of catalyst material 1.1 was set at a temperature (455° C.) to provide for ~50% conversion (with residual oxygen content of 2.06 mol. %). Conversion (upper panel) remained essentially constant throughout, with minimal deviation (±1-2° C.), similar to catalyst 1.6. Selectivity showed a gradual increase over time, moving from ~88% to ~90%. The results indicate that rate that precipitated silica is compatible for use as a support, as it demonstrates good conversion and selectivity at temperatures over 400° C. that is maintained for at least 48 hours.

Figure 6:
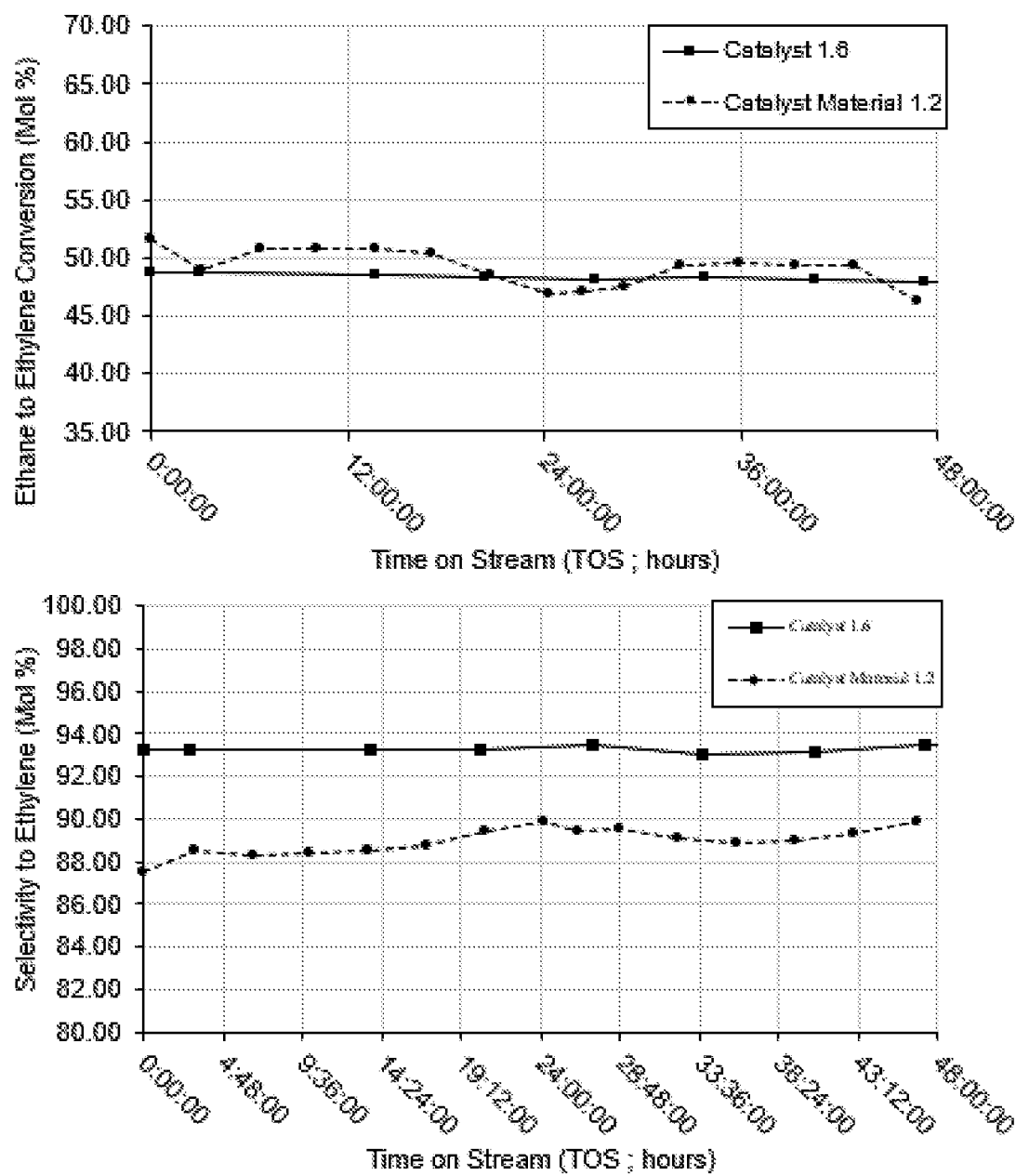
FIG. 6 shows plots of conversion and selectivity as a function of time for catalyst material 1.2 (including catalyst 1.6 included for comparison) while maintaining operating temperature at 450° C. to provide for 50% conversion.

FIG. 6 shows the effect of long-term testing for catalyst material 1.2, with results for catalyst 1.6 included for comparison, with a time on stream (TOS) of ~48 hours. The starting temperature for robustness testing of catalyst material 1.2 was set at a temperature (450° C.) to provide for ~50% conversion (with residual oxygen content of 2.40 mol. %). Conversion (upper panel) remained essentially constant throughout, with minimal deviation (±1-2° C.), similar to catalyst 1.6. Selectivity showed a gradual increase over time, moving from −88% to ~90%. The results indicate that rate that fumed silica is compatible for use as a support.

Results for catalyst materials 1.3, 1.4, and 1.5 demonstrated similar results for robustness, with a slight decline in conversion before stabilizing over time. The temperatures used were slightly higher, set at 460° C., which may account for the decrease. Despite the slight decreases, these catalyst materials demonstrate an ability to maintain relatively high selectivity (~90%) at temperatures over 450° C. Operating at lower temperatures, such as 430° C., would likely result in stable conversion rates and possibly higher selectivity.

In contrast, catalyst materials 2.1, 2.3, 2.4 and 2.5 demonstrated poor performance as conversion dropped significantly during testing, or selectivity was reduced to levels as low as 65%. The overall results of robustness testing are summarized in Table 3 below.

Acetic Acid Production

Acetic acid selectivity was determined by running MRU testing long enough to collect an aqueous condensate in the condenser (e.g., 1-5 days) downstream of the MRU. After collecting a sample of the condensate, the sample was submitted for liquid GC analysis (Agilent 6890N Gas Chromatograph, Using Chrom Perfect—Analysis, Version 6.1.10 for data evaluation). To perform the liquid GC analysis, 300-450 mg of liquid sample was transferred to a scintillation vial. Next, 25 mg of isopropanol (IPA) was added as an internal standard. Furthermore, 18-20 mL of distilled $H_2O$ was added to dilute the sample. Prepared samples were then transferred to GC vials and set in sequence to be tested using an auto sampler. The GC analysis was a split injection method with a temperature program and FID detector. Furthermore, a set of 3 calibration standards were run in duplicate for the relative response factor used for calculating acetic acid content in the sample.

Corresponding wt. % acetic acid levels, as measured by GC analysis, in aqueous condensate product from MRU long-term robustness testing data for Catalysts 1.1, 1.5, & 1.6 and Catalyst Materials 1.1-1.5, 2.3 & 2.5 is shown in Table 4 below. The aqueous condensate sample was collected on the indicated day, which allowed for sufficient quantity of liquid to be collected and subsequently quantified by GC analysis. Measurement of acetic acid using GC analysis of aqueous condensate was necessary due to the small scale of the MRU apparatus. On a commercial scale the amount of aqueous acetic acid would be large enough so that mass balance calculations could be used on the gaseous product stream to measure acetic acid levels with a high level of accuracy. Use of GC analysis provided accurate measurements of acetic acid levels, in wt. %, of the entire reactor effluent. It should be noted, that the selectivity calculations did not include the acetic acid component, which was not part of the gaseous phase.

TABLE 4

| Catalyst/ Catalyst Material | Sample Collection Day | MRU Process Temp (° C.) | Acetic Acid (wt. %) | Conversion (%) | Selectivity (%) |
| --- | --- | --- | --- | --- | --- |
| Catalyst 1.1 | 2nd day | 440 | 1.95 | 48.2 ± 1.8 | 91.3 ± 0.4 |
| Catalyst 1.1 | 3rd day | 448 | 2.12 | 49.0 ± 2.3 | 91.3 ± 0.5 |
| Catalyst 1.5 | 5th day | 465 | 1.20 | 54.6 ± 4.7 | 90.3 ± 0.7 |
| Catalyst 1.5 | 6th day | 465 | 1.10 | | |

TABLE 3

| Catalyst Material | Temp. (° C.) | TOS (hrs) | Conversion (%) Starting/End | Trend | Selectivity (%) Starting/End | Trend |
| --- | --- | --- | --- | --- | --- | --- |
| 1.1 | 455 | 48 | 50/50 | Stable | 88/90 | Gradual increase |
| 1.2 | 450 | 48 | 52/49 | Fluctuating but stable | 87/90 | Gradual increase |
| 1.3 | 460 | 48 | 50/46 | Slow decline to stable | 91/90 | Stable |
| 1.4 | 460 | 39 | 53/43 | Slow decline to stable | 91/91 | Stable |
| 1.5 | 460 | 39 | 50/44 | Slow decline to stable | 88/87 | Stable |
| 2.1 | 460 | 19.5 | 48/46 | Stable | 81/80 | Stable |
| 2.3* | 440 | 76 | 45/35 | Initial drop to steady | 77/65 | Rapid decline |
| 2.4 | 470 | 15 | 50/28 | Steady decline | 82/86 | Gradual increase |
| 2.5 | 438 | 65 | 40/43 | Slow decline | 87/83 | Initial drop to stable |

TABLE 4-continued

| Catalyst/Catalyst Material | Sample Collection Day | MRU Process Temp (° C.) | Acetic Acid (wt. %) | Conversion (%) | Selectivity (%) |
|---|---|---|---|---|---|
| Catalyst 1.6 | 5th day | 470 | 2.80 | 62.6 ± 2.3 | 90.3 ± 0.3 |
| Catalyst 1.6 | 6th day | 455 | 3.30 | 52.7 ± 0.6 | 90.2 ± 0.4 |
| Catalyst 1.6 | 2nd day | 442 | 2.00 | 48.0 ± 0.7 | 93.3 ± 0.2 |
| Catalyst 1.6 | 3rd day | 442 | 2.60 | | |
| Catalyst Material 1.1 | 2nd day | 455 | 1.23 | 50.1 ± 1.2 | 88.8 ± 1.0 |
| Catalyst Material 1.2 | 2nd day | 450 | 2.00 | 48.9 ± 2.7 | 88.7 ± 1.2 |
| Catalyst Material 1.3 | 2nd day | 460 | 0.97 | 45.8 ± 3.4 | 90.1 ± 0.4 |
| Catalyst Material 1.3 | 3rd day | 460 | 0.97 | | |
| Catalyst Material 1.4 | 2nd day | 460 | 0.80 | 47.3 ± 4.3 | 90.7 ± 0.6 |
| Catalyst Material 1.4 | 3rd day | 460 | 0.70 | | |
| Catalyst Material 1.5 | 2nd day | 460 | 0.70 | 46.0 ± 3.6 | 87.1 ± 0.8 |
| Catalyst Material 1.5 | 3rd day | 460 | 0.60 | | |
| Catalyst Material 2.3 | 4th day | 440 | 1.78 | 39.6 ± 5.2 | 70.6 ± 7.0 |
| Catalyst Material 2.5 | 2nd day | 438 | 0.92 | 47.7 ± 5.2 | 84.4 ± 2.7 |

The results demonstrate that acetic acid levels, despite showing some day-to-day variability, do not exceed 3.5 wt. %. This is quite low, particularly considering that the measurements were taken when conversion levels were close to 50%. Many ODH catalysts known in the art have demonstrated acetic acid selectivities ranging from 5 to 12 wt. %.

Physical Characterization

Physical characterization of the catalysts and catalyst materials produced was performed to determine molar ratios of the elements present, the phase composition (particularly in relation to the M1 and amorphous phases), and for particle size.

SEM

Figure 7:
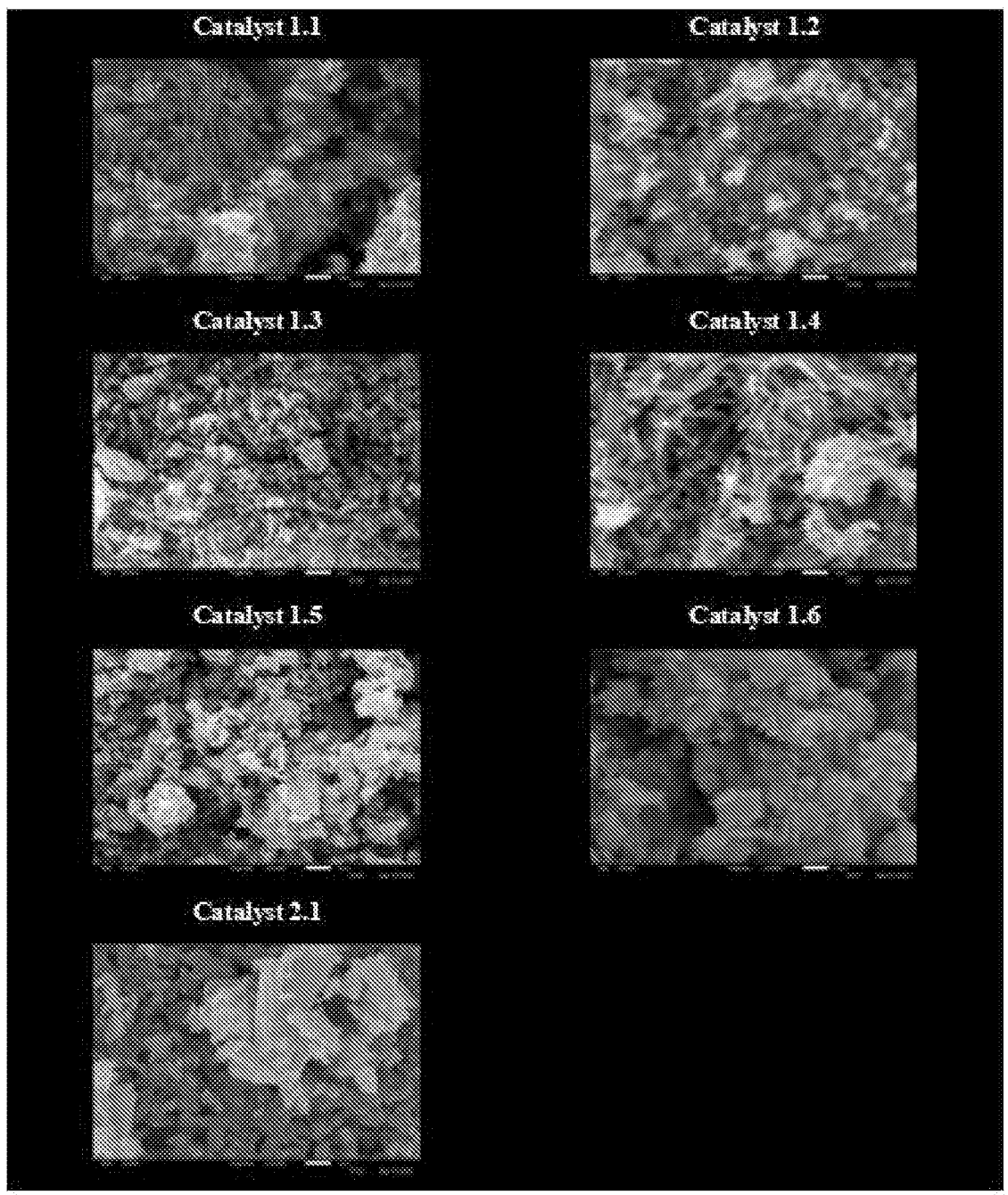
FIG. 7 shows scanning electron microscope (SEM) images for catalysts 1.1-1.6, and 2.1 at 10,000× magnification.
Figure 8:
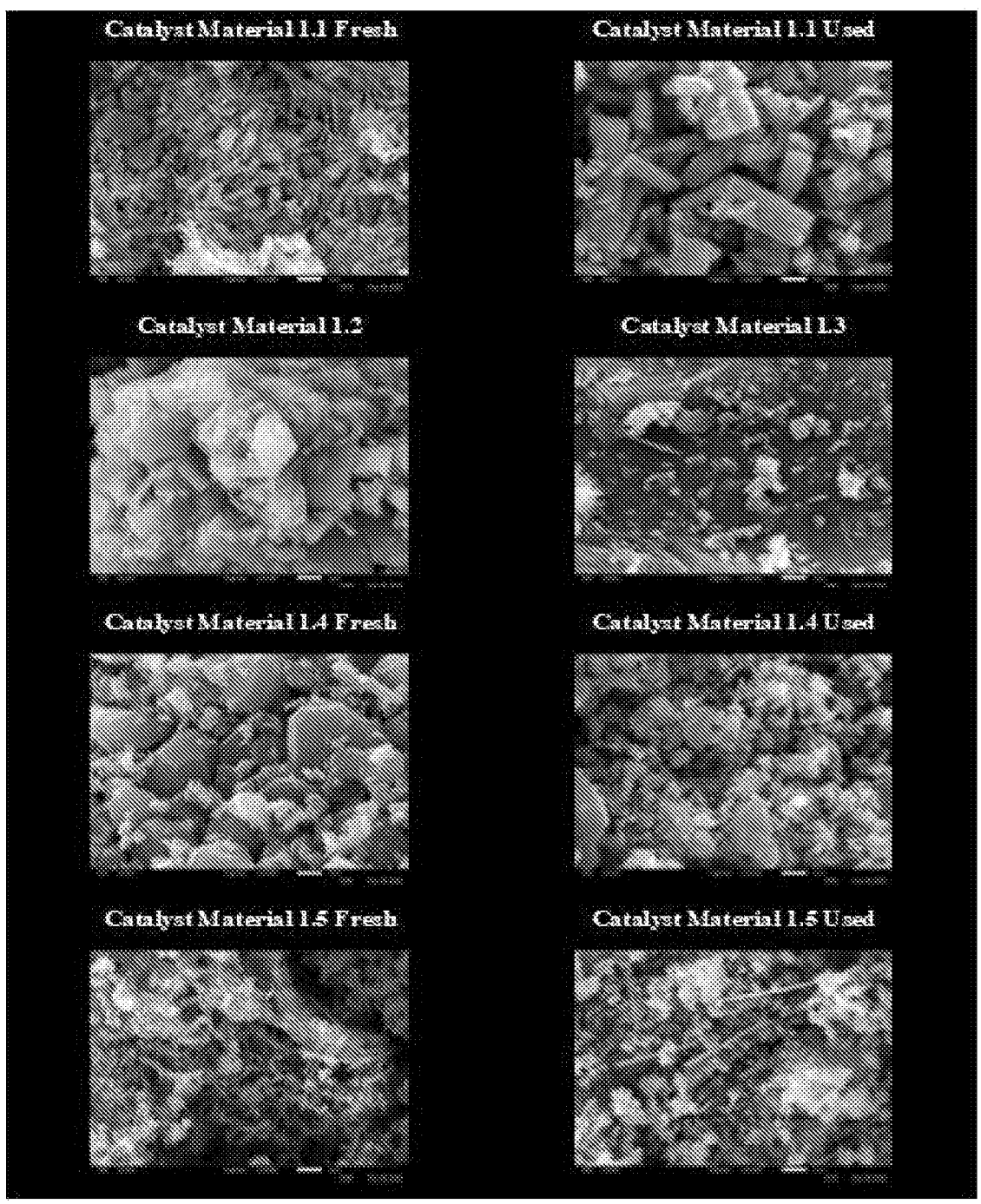
FIG. 8 shows SEM images for fresh and used catalyst materials 1.1, 1.4, and 1.5, and for fresh catalyst materials 1.2 and 1.3 at 10,000× magnification.

Scanning electron microscope (SEM) images were collected using a JSM-IT300LV InTouchScope™. The sample is prepared on an aluminum stud with double sided carbon tape. This sample is scanned on an SEM stage. FIG. 7 includes SEM images (10,000× magnification) for catalysts 1.1-1.6, and 2.1. The difference in appearance of catalyst 2.1 compared to catalysts 1.1-1.6 suggest different crystal structures, which may account for the significant differences in conversion and selectivity. FIG. 8 includes SEM images (10,000× magnification) for fresh and used catalyst materials 1.1, 1.4, and 1.5, and for fresh catalyst materials 1.2 and 1.3.

SEM-EDS

Energy-dispersive X-ray spectroscopy (EDS) was conducted using a JEOL JED-2300 DRY SDD EDS detector. Samples were sent to SEMx Incorporated for EDS analysis to determine the molar ratios of the elements present in the catalysts and catalyst materials. Tested catalyst and catalyst material samples were finely ground to reduce particle size and obtain a uniform mixture. They were then loaded onto EDS stub for analysis by SEM. EDS was used for elemental analysis and surface examination. EDS is a micro-analytical technique that provides a semi-quantitative elemental analysis of the surface of a sample (e.g. the top 1 to 3 microns). The SEM is used to examine the surface morphology at magnifications ranging from 20 to 100,000 times. The EDS instrument can detect elements with an atomic number equal or greater than sodium, but also has light element capability, which means that it can also detect carbon, nitrogen, oxygen, and fluorine. The estimated lower detectable limit for any given element generally is between about 0.2 and 0.5 wt. %.

EDS assessments of prepared catalysts to determine the elemental composition was performed on the catalysts and catalyst materials. The EDS elemental mass wt. % for detected elements was using to determine molar ratios, shown in Table 5. Catalysts 1.1-1.6 are significantly different than the comparative example catalyst 2.1. Relative to the molybdenum component, V is significantly higher and Te is significantly lower. The tantalum levels are typically higher, with exceptions for catalysts 1.5 and 1.6.

TABLE 5

| | EDS Measured Elemental Mass wt. % | | | | Chemical Formula |
|---|---|---|---|---|---|
| Catalyst | Mo | V | Te | Ta | (mol ratio) |
| 1.1 | 40.54 | 8.64 | 6.69 | 11.85 | $Mo_1V_{0.40}Te_{0.12}Ta_{0.15}$ |
| 1.2 | 43.33 | 10.08 | 1.39 | 10.66 | $Mo_1V_{0.44}Te_{0.02}Ta_{0.13}$ |
| 1.3 | 39.41 | 8.12 | 8.39 | 10.97 | $Mo_1V_{0.39}Te_{0.16}Ta_{0.15}$ |
| 1.4 | 38.93 | 9.40 | 8.74 | 10.38 | $Mo_1V_{0.45}Te_{0.17}Ta_{0.14}$ |
| 1.5 | 42.61 | 11.13 | 9.23 | 4.82 | $Mo_1V_{0.49}Te_{0.16}Ta_{0.06}$ |
| 1.6 | 42.03 | 10.96 | 8.44 | 5.50 | $Mo_1V_{0.49}Te_{0.15}Ta_{0.07}$ |
| 2.1 | 41.96 | 6.65 | 14.59 | 4.95 | $Mo_1V_{0.30}Te_{0.26}Ta_{0.06}$ |

EDS determination of molar ratios of catalyst materials was also performed, with results shown in Table 6. The identification of additional elements, such as Si, Al, Na, and Mg, likely contributions from support materials, are also noted in the chemical formulas. The tendency of some catalysts to lose activity or selectivity over time may be due to the change in the composition under oxidative dehydrogenation process conditions. Several catalyst materials were reassessed (labeled as "used") with EDS following use for robustness testing to ascertain whether there is a significant change in the composition. No significant changes in the four elements Mo, V, Te, and Te were observed. The appearance of low levels of iron in used catalyst materials may be due to leaching of iron from the reactor tubing.

TABLE 6

| Sample | EDS Determined Catalyst Chemical Formula (mol ratio) |
|---|---|
| Catalyst Material 1.1 | $Mo_1V_{0.43}Te_{0.15}Ta_{0.07}Si_{5.14}Al_{0.03}$ |
| Catalyst Material 1.1 (used) | $Mo_1V_{0.47}Te_{0.16}Ta_{0.11}Si_{5.79}Al_{0.07}Fe_{0.01}$ |
| Catalyst Material 1.2 | $Mo_1V_{0.47}Te_{0.16}Ta_{0.11}Si_{2.44}Al_{0.03}$ |
| Catalyst Material 1.3 | $Mo_1V_{0.43}Te_{0.15}Ta_{0.09}Si_{1.83}Al_{0.15}Fe_{0.02}Na_{0.02}Mg_{0.01}$ |
| Catalyst Material 1.4 | $Mo_1V_{0.50}Te_{0.16}Ta_{0.11}Si_{0.04}Al_{2.68}$ |
| Catalyst Material 1.4 (used) | $Mo_1V_{0.50}Te_{0.16}Ta_{0.11}Si_{0.04}Al_{2.10}$ |
| Catalyst Material 1.5 | $Mo_1V_{0.54}Te_{0.16}Ta_{0.10}Si_{0.04}Al_{0.04}Ti_{5.17}$ |
| Catalyst Material 1.5 (used) | $Mo_1V_{0.51}Te_{0.17}Ta_{0.08}Si_{0.03}Al_{0.05}Ti_{6.85}$ |

PSD by SEM

Samples were sent to SEMx Incorporated for particle size analysis using scanning electron microscopy (SEM), model JEOL-JSM300 LV. SEM was used to observe and count the particles in the sample to obtain the Particle Size Distribution (PSD). For the PSD measurements, the SEM instrument took pictures at different magnifications. Measurements were done for 400-800 particles at different magnifications to cover the size range (statistical population). Size was measured by length in micrometers on the longest dimension of the particles. SEM based PSD is the preferred method for analyzing samples where particles are agglomerated (stuck together) because the analyst can visually see this through the microscope and make the judicious decision to measure the distinct particles rather than the agglomerates. Statistics and analyses were based on total counts measured by SEM.

Particle size distribution results for catalysts 1.1 to 1.6, and 2.1 are shown in Table 7 and for catalyst materials 1.1 and 1.2 in Table 8.

Nitrogen physisorption experiments were performed on a TriStar (Micromeritics Instruments), with samples undergoing analysis by nitrogen adsorption at 77 K. The samples were loaded into physisorption cells and degassed at 200° C. for 1 h prior to the adsorption experiments.

Surface area and pore volume measurements for catalyst 1.6 and catalyst 2.1 are shown in Table 9.

TABLE 7

| Catalyst | Size (um) | | | | | | | | |
|---|---|---|---|---|---|---|---|---|---|
| | D10 | D25 Quartile 1 | D50 Median | D75 Quartile 3 | D90 | Max. | Min. | Mean | Mode |
| 1.1 | 0.34 | 0.87 | 6.60 | 15.00 | 33.61 | 377.50 | 0.11 | 15.23 | 8.75-11.16 |
| 1.2 | 0.18 | 0.28 | 2.37 | 11.11 | 26.25 | 163.75 | 0.08 | 9.15 | 0.18-0.23 |
| 1.3 | 0.21 | 0.40 | 1.20 | 4.75 | 10.09 | 77.80 | 0.06 | 3.60 | 0.47-0.60 |
| 1.5 | 0.26 | 0.41 | 1.21 | 3.40 | 16.67 | 74.00 | 0.07 | 4.93 | 0.29-0.37 |
| 1.6 | 0.30 | 0.54 | 1.18 | 2.17 | 4.57 | 150.22 | 0.12 | 2.87 | 0.98-1.25 |
| 2.1 | 0.20 | 0.27 | 0.46 | 1.12 | 4.03 | 387.27 | 0.08 | 3.09 | 0.23-0.29 |

TABLE 8

| Catalyst Material | Size (um) | | | | | | | | |
|---|---|---|---|---|---|---|---|---|---|
| | D10 | D25 Quartile 1 | D50/ Median | D75/ Quartile 3 | D90 | Max. | Min. | Mean | Mode |
| 1.1 | 0.99 | 15.00 | 27.22 | 40.57 | 53.00 | 160.02 | 0.08 | 28.02 | 29.52-37.64 |
| 1.2 | 0.38 | 1.60 | 21.67 | 76.67 | 132.20 | 1228.07 | 0.05 | 51.05 | 99.60-127.02 |

Pore Volume, BET Surface Area Analysis and BJH Pore Size Distribution Analysis

Gas adsorption manometry was used for the determination of adsorption isotherms of nitrogen at the temperature of liquid nitrogen (~77 K). The amount of gas adsorbed was evaluated by measuring the change in gas pressures. Isothermal nitrogen adsorption processes are measured, and surface areas and volumes were calculated through the application of various theories/equations.

Total pore volume was calculated by nitrogen gas uptake at the relative pressure $P/P_0 = 0.99$.

Brunauer-Emmett-Teller (BET) analysis was applied to quantify the specific surface area ($m^2/g$) of the solid samples. BET valuations were performed by multilayer adsorption of nitrogen and measured as a function of relative pressure. Since different solids can have drastically different isotherm shapes, they are difficult to compare. Applying BET theory allows for a more quantitative comparison of solids' surface areas by determining the so-called monolayer capacity from nitrogen multilayer adsorption experiment. Monolayer capacity is a representation of total specific surface area and encompasses both the external area and pore area of porous solid.

Barrett-Joyner-Halenda (BJH) method was used for calculating pore size (Å) distributions from experimentally collected adsorption isotherms using the Kelvin model of pore filling ($cm^3/g \cdot A$). This technique characterizes pore size distribution independently of external area due to particle size of the sample and can be applied to mesopore and small macropores.

TABLE 9

| Sample | BET Surface Area ($m^2/g$) | Pore Volume ($cm^3/g$) |
|---|---|---|
| Catalyst 1.6 | 4 | 0.03 |
| Catalyst 2.1 (comparative) | 1 | 0.01 |

XRD

X-Ray Diffractometry (XRD) data was collected using a PANalytical Aeris X-ray diffractometer by SEMx Incorporated. The data was used to determine the phase compositions present in the prepared catalysts. The diffractometer instrument consisted of three basic elements: X-ray tube, sample holder, and X-ray detector. X-rays are generated in a cathode ray tube (Cu source with Kα radiation=1.5418 Å) with the resulting X-rays being directed onto the sample. As the sample and detector are rotated, the intensity of the reflected X-rays is recorded to produce characteristic X-ray spectra. When the incident X-rays reflecting off the sample satisfies the Bragg Equation ($n\lambda = 2d \sin \theta$), constructive interference occurs and a peak in intensity occurs (y-axis). X-ray diffractometers are setup such that the sample rotates in the path of the X-ray beams at an angle θ, while the X-ray detector is mounted on an arm to collect the diffracted X-rays and rotates at an angle of 2θ from ~5° to 70° (x-axis).

Qualitative XRD analysis and Rietveld Refinement was performed using HighScore Plus XRD analysis software. The samples were finely ground to reduce particle size and to obtain a uniform mixture. They were then loaded onto the XRD sample holder and the XRD spectrum was acquired. The Rietveld Refinement results were combined with Highscore Plus and EDS results to perform qualitative and quantitative analysis.

Amorphous Content Determination

The weight percentage of amorphous content was determined by external standard. With an external standard phase, the instrument intensity constant, K-factor, was determined. Corundum was used as the external standard and was measured with the same instrument configuration shortly after the unknown sample was measured. The K-factor approach is described by O'Connor and Raven: 1988, Powder Diffraction, 3 (1), 2-6. For each sample, the weight percentage of the crystalline MoTeVTaO orthorhombic phase had to be determined in order to assign weight percentages to the amorphous content. The Degree of Crystallinity (DOC) Method, based on the estimation that the total intensity of area contributed to the overall diffraction pattern by each component in the analysis, was used to determine the amount of amorphous phase. The degree of crystallinity is calculated from the total areas under the defined crystalline and amorphous components from:

DOC=Crystalline Area Crystalline Area+Amorphous Area

Where the weight fraction of the amorphous material can be calculated from:

$W$amorphous=1−DOC

The ortho-MoTeVTaO$_x$ phase contributed to the crystalline area and therefore needed to be quantified in order to determine the amorphous area. To compensate for the fact that different materials and backgrounds would have different effects, a sample of orthorhombic, Pba2 MoVTeNbO$_x$ phase was used to calibrate some constants needed for the DOC method. Samples containing MoTeVTaO$_x$ orthorhombic Pba2 phase had this phase weight percentages determined semi-quantitative based on the MoVTeNbO$_x$ calibration.

M1 Phase Content Determination

The MoTeVTaO$_x$ orthorhombic, Pba2 phase (also referred to in literature as the M1 phase) was fitted using literature crystal structure data for a different yet crystallographically analogous compound since its orthorhombic Pba2 crystalline phase was a match. See DeSanto. P, Jr & Buttrey, D. & Grasselli, R. & Pyrz, W. & Lugmair, C. & F, Jr & Vogt, Thomas & Toby, Brian. (2006). *Topics in Catalysis* 38:31-40 ("DeSanto").

Lattice parameters: a=21.14(2) Å, b=26.66(3) Å, c=4.008 Å

Comparative Raw Data Analysis

Rietveld refinement for phase identification for catalysts 1.1-1.6, and 2.1 and associated wt. % for identified phases is shown in Table 10. The 9 digits codes located under the phase chemical formulae represent corresponding reference codes from the PDF-4+2020. Phase (TeO)$_{0.43}$((Mo$_{4.08}$V$_{0.70}$Ta$_{0.22}$)O$_{14}$) corresponds to a phase identified in DeSanto. The M1 phase, represented by (TeO)$_{0.43}$((Mo$_{4.08}$V$_{0.70}$Ta$_{0.22}$)O$_{14}$), was not detected in catalyst 1.2, and was significantly lower in catalyst 2.1 which was synthesized following the methodology disclosed in US20100222623. The results, in view of the performance results, indicate that a significant M1 phase is essential for achieving high conversion and selectivity, even at temperatures above 400° C. Furthermore, the most active catalysts include an amorphous phase of at least 26.9, with the majority of the examples comprising an amorphous phase of from 34.2 to 48.9.

TABLE 10

| Phase | Catalyst 1.1 | Catalyst 1.2 | Catalyst 1.3 | Catalyst 1.4 | Catalyst 1.5 | Catalyst 1.6 | Catalyst 2.1 |
|---|---|---|---|---|---|---|---|
| (Mo$_{1.83}$V$_{1.17}$)Te$_{0.88}$O$_{9.25}$ 01-081-9132 | 5.1 | — | 16.4 | 17.4 | 26.5 | 18.3 | 33.8 |
| (TeO)$_{0.43}$((Mo$_{4.08}$V$_{0.70}$Ta$_{0.22}$)O$_{14}$) | 15.6 | — | 23.8 | 13.7 | 16.4 | 16.1 | 0.8 |
| Mo$_5$TeO$_{16}$ 04-014-0572 | 4.8 | 0.6 | 0.8 | 4.4 | — | 1.0 | 25.9 |
| (VO)MoO$_4$ 01-074-1508/04-008-7126 | 4.9 | 9.8 | 5.5 | 8.6 | 8.8 | 16.5 | 2.9 |
| V$_{1.1}$Mo$_{0.9}$O$_5$/V$_{0.95}$Mo$_{0.97}$O$_5$ 04-013-6424/01-077-0649 | 5.1 | 14.5 | 2.3 | 4.8 | 6.5 | 3.1 | 3.1 |
| Ta$_2$O$_5$ 04-011-7458/01-073-2323 | 1.9 | 0.2 | 0.5 | 0.7 | — | 0.5 | 2.4 |
| TaO$_2$ 04-003-1862/00-019-1297 | — | — | 1.4 | 2.2 | 1.3 | 0.2 | — |
| Ta$_{1.10}$O$_{1.05}$/Ta$_{1.08}$O 04-007-2331/04-009-7272 | 0.7 | 1.9 | 1.6 | 1.0 | — | — | 1.0 |
| TeO$_2$ 04-007-2021/04-003-1862/ 04-003-5854/03-065-2835 | 1.3 | 1.1 | 0.9 | 1.1 | 0.4 | 0.2 | 0.9 |
| Mo$_{17}$O$_{47}$ 04-005-7144 | — | — | — | — | — | — | 1.9 |
| Mo$_5$O$_{14}$ 04-007-2157 | 7.5 | 27.9 | 5.5 | 7.0 | 6.5 | 9.1 | — |
| Other Mixed Metal Oxide or Metal Oxide Phases | 4.1 | 8.0 | 3.0 | 1.7 | 6.7 | 0.8 | 1.4 |
| Amorphous | 48.9 | 36.1 | 38.3 | 37.3 | 26.9 | 34.2 | 25.7 |
| Total | 99.8 | 100.1 | 100.0 | 99.9 | 100.0 | 100.0 | 99.8 |

Rietveld Refinement for phase identification for Catalyst Materials 1.1-1.5 and associated wt. % for identified phases is shown in Table 11 below. The 9 digits codes located under the phase chemical formulae represent corresponding reference codes from the PDF-4+2020. Phase (TeO)$_{0.43}$((Mo$_{4.08}$V$_{0.70}$Ta$_{0.22}$)O$_{14}$) corresponds to a phase identified in DeSanto.

The results show that the suspected M1 phase, (TeO)$_{0.43}$((Mo$_{4.08}$V$_{0.70}$Ta$_{0.22}$)O$_{14}$), while reduced compared to catalyst 1.6, is still higher than the comparative catalyst 2.1 (see Table 10). This suggests that a catalyst material having an M1 phase of at least 2.5 wt. % or greater will provide good conversion and selectivity at temperatures over 400° C. Further, the combining of the catalyst support/carriers listed in Table 2 and used for catalysts 1.1, 1.2, 1.4, and 1.5 are not likely to reduce the M1 phase to a level where conversion and selectivity are compromised.

TABLE 11

| Phase | Catalyst 1.6 | Catalyst Material 1.1 | Catalyst Material 1.2 | Catalyst Material 1.4 | Catalyst Material 1.5 |
| --- | --- | --- | --- | --- | --- |
| $(Mo_{1.83}V_{1.17})Te_{0.88}O_{9.25}$ 01-081-9132 | 18.3 | 3.76 | 8.5 | 14.4 | 9.5 |
| $(TeO)_{0.43}((Mo_{4.08}V_{0.70}Ta_{0.22})(O_{14})$ | 16.1 | 2.79 | 3.9 | 10.2 | 7.1 |
| $Mo_5TeO_{16}$ 04-014-0572 | 1.0 | — | — | — | — |
| $(VO)MoO_4$ 01-074-1508/04-008-7126 | 16.5 | 0.77 | 1.1 | 3.8 | 3.7 |
| $V_{1.1}Mo_{0.9}O_5/V_{0.95}Mo_{0.97}O_5$ 04-013-6424/01-077-0649 | 3.1 | 0.09 | 0.7 | 0.8 | 0.5 |
| $Ta_2O_5$ 04-011-7458/01-073-2323 | 0.5 | 0.01 | 0.04 | — | 0.1 |
| $TaO_2$ 04-003-1862/00-019-1297 | 0.2 | — | 0.1 | — | — |
| $TeO_2$ 04-007-2021/04-003-1862/ 04-003-5854/03-065-2835 | 0.2 | — | — | — | — |
| $Mo_5O_{14}$ 04-007-2157 | 9.1 | 0.31 | 2.0 | 3.7 | 3.3 |
| Support Phases | — | 0.93 | 2.1 | 57.1 | 41.9 |
| Other Mixed Metal Oxide or Metal Oxide Phases | 0.8 | 0.23 | 0.7 | — | — |
| Amorphous | 34.2 | 91.11 | 80.9 | 10.0 | 33.9 |
| Total | 100.0 | 100.0 | 100.04 | 100.0 | 100.0 |

Table 12 includes Rietveld Refinements for phase identification and associated wt. % for identified phases for select catalyst materials before and after MRU testing. The 9 digits codes located under the phase chemical formulae represent the corresponding reference codes from the PDF-4+2020. Phase $(TeO)_{0.43}((Mo_{4.08}V_{0.70}Ta_{0.22})O_{14})$ corresponds to a phase identified in DeSanto. These results indicate that the M1 phase does not change significantly over time, which may explain the robustness demonstrated by these catalyst materials.

TABLE 12

| Phase | Catalyst Material 1.1 Fresh | Catalyst Material 1.1 Used | Catalyst Material 1.4 Fresh | Catalyst Material 1.4 Used | Catalyst Material 1.5 Fresh | Catalyst Material 1.5 Used |
| --- | --- | --- | --- | --- | --- | --- |
| $(Mo_{1.83}V_{1.17})Te_{0.88}O_{9.25}$ 01-081-9132 | 3.76 | 5.6 | 14.4 | 13.5 | 9.5 | 8.3 |
| $(TeO)_{0.43}((Mo_{4.08}V_{0.70}Ta_{0.22})O_{14})$ | 2.79 | 3.0 | 10.2 | 12.2 | 7.1 | 5.3 |
| $(VO)MoO_4$ 01-074-1508/04-008-7126 | 0.77 | 0.3 | 3.8 | 2.3 | 3.7 | 1.3 |
| $V_{1.1}Mo_{0.9}O_5/V_{0.95}Mo_{0.97}O_5$ 04-013-6424/01-077-0649 | 0.09 | 0.8 | 0.8 | 0.7 | 0.5 | 0.9 |
| $Ta_2O_5$ 04-011-7458/01-073-2323 | 0.01 | — | — | — | 0.1 | — |
| $Mo_5O_{14}$ 04-005-7144 | 0.31 | 1.5 | 3.7 | 3.3 | 3.3 | 1.8 |
| Support phases | 0.93 | 39.3 | 57.1 | 46.1 | 41.9 | 46.5 |
| Other Mixed Metal Oxide or Metal Oxide Phases | 0.23 | — | — | — | — | 0.1 |
| Amorphous | 91.11 | 49.4 | 10.0 | 21.8 | 33.9 | 35.8 |
| Total | 100.0 | 99.9 | 100.0 | 99.9 | 100.0 | 100.0 |

Figure 9:
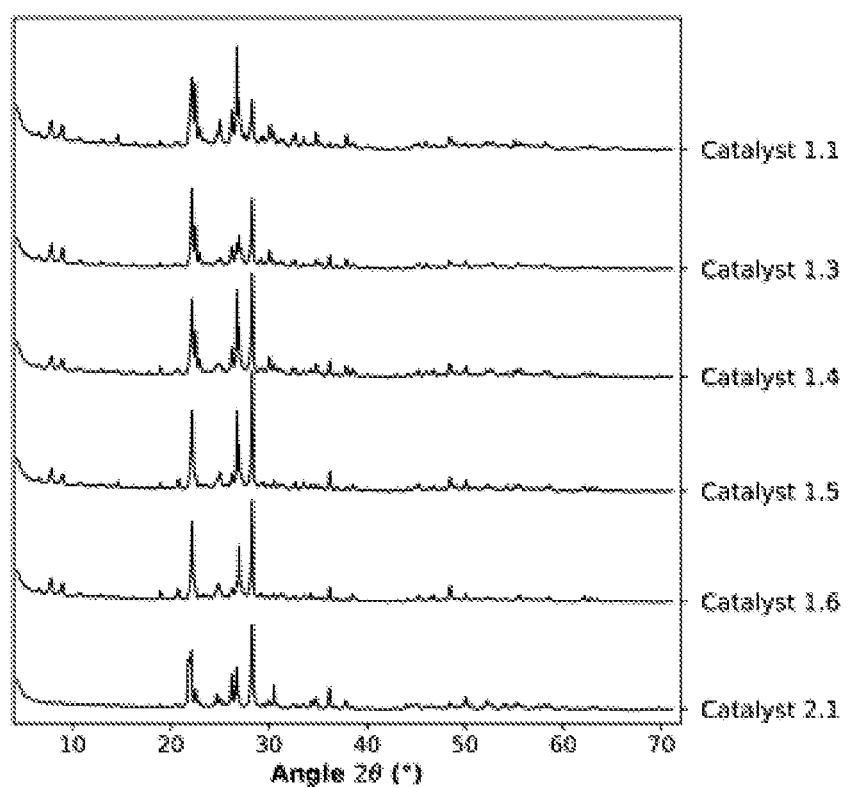
FIG. 9 shows X-Ray Diffractometry (XRD) spectra for catalysts 1.1, 1.3-1.6, and 2.1.

FIG. 9 represents plots of XRD spectra (normalized to the peak near 22.2°) for catalysts 1.1, 1.3, 1.4, 1.5, and 1.6, and for comparison catalyst 2.1. Relative peak intensity and 2θ angle ranges for peaks identified in FIG. 9 for catalysts 1.1, 1.3, 1.4, 15, and 1.6 (composite) are shown in Table 13. The peaks correlate to a general pattern that is determined by the crystal structure. Key peaks include peaks near 22.2°, 26.7°, and 28.3° which demonstrate a max intensity of at least 100%. Additional peaks that should be noted include peaks near 7.8°, 9.0°, 22.9°, and 25.0°. Catalyst 2.1 shares some similarities but is missing peaks near 7.8° and 9.0°.

TABLE 13

| Min Angle (2θ) | Max Angle (2θ) | Min Intensity | Max Intensity |
| --- | --- | --- | --- |
| 6.60 | 6.65 | 33.6% | 45.4% |
| 7.79 | 7.86 | 42.2% | 56.3% |

TABLE 13-continued

| Min Angle (2θ) | Max Angle (2θ) | Min Intensity | Max Intensity |
| --- | --- | --- | --- |
| 8.98 | 9.02 | 36.9% | 52.7% |
| 10.72 | 10.74 | 28.9% | 39.7% |
| 12.98 | 13.03 | 27.1% | 38.7% |
| 13.93 | 14.00 | 25.2% | 35.5% |

TABLE 13-continued

| Min Angle (2θ) | Max Angle (2θ) | Min Intensity | Max Intensity |
|---|---|---|---|
| 14.57 | 14.61 | 26.5% | 42.8% |
| 16.15 | 16.20 | 24.7% | 34.8% |
| 17.71 | 17.76 | 22.9% | 34.9% |
| 18.97 | 18.99 | 25.9% | 37.0% |
| 19.45 | 19.61 | 23.2% | 32.4% |
| 20.02 | 20.09 | 23.1% | 32.5% |
| 20.77 | 20.82 | 25.3% | 36.2% |
| 22.16 | 22.18 | 100.0% | 100.0% |
| 22.47 | 22.55 | 36.5% | 93.7% |
| 22.95 | 22.97 | 26.9% | 50.5% |
| 23.59 | 23.68 | 26.2% | 37.7% |
| 24.82 | 25.04 | 30.9% | 57.3% |
| 26.21 | 26.25 | 34.0% | 67.0% |
| 26.71 | 26.73 | 40.3% | 131.3% |
| 26.95 | 26.98 | 53.9% | 77.9% |
| 28.27 | 28.30 | 76.4% | 138.1% |
| 29.18 | 29.24 | 28.5% | 40.4% |
| 30.06 | 30.10 | 25.5% | 53.1% |
| 30.50 | 30.54 | 28.6% | 46.2% |
| 31.27 | 31.38 | 27.1% | 39.1% |
| 32.70 | 32.72 | 26.6% | 44.6% |
| 33.51 | 33.55 | 25.4% | 40.1% |
| 34.26 | 34.30 | 24.5% | 34.3% |
| 34.83 | 34.85 | 25.2% | 45.2% |
| 35.34 | 35.40 | 24.6% | 34.6% |
| 36.17 | 36.22 | 32.9% | 39.4% |
| 36.90 | 36.94 | 23.5% | 33.8% |
| 37.36 | 37.45 | 21.8% | 31.1% |
| 37.91 | 37.93 | 23.6% | 42.6% |
| 38.50 | 38.59 | 24.9% | 34.8% |
| 39.98 | 40.07 | 21.7% | 32.0% |
| 41.58 | 41.65 | 21.2% | 29.7% |
| 42.99 | 43.08 | 21.7% | 30.4% |
| 44.00 | 44.16 | 21.6% | 31.4% |
| 45.24 | 45.30 | 26.1% | 35.1% |
| 45.83 | 46.01 | 22.3% | 36.5% |
| 46.78 | 46.84 | 23.9% | 33.1% |
| 47.61 | 47.68 | 22.7% | 32.4% |
| 48.45 | 48.45 | 28.1% | 41.0% |
| 50.05 | 50.08 | 28.2% | 35.0% |
| 50.98 | 51.18 | 23.5% | 32.9% |
| 52.23 | 52.28 | 24.1% | 36.3% |
| 52.76 | 52.83 | 23.4% | 36.2% |
| 54.17 | 54.28 | 23.5% | 33.0% |
| 55.03 | 55.05 | 22.6% | 37.7% |
| 55.38 | 55.55 | 26.4% | 35.2% |
| 58.11 | 58.15 | 22.9% | 35.5% |
| 58.50 | 58.72 | 23.4% | 31.8% |
| 62.07 | 62.11 | 22.2% | 31.1% |
| 62.79 | 62.81 | 22.2% | 32.6% |
| 63.41 | 63.47 | 21.7% | 30.6% |

Figure 10:
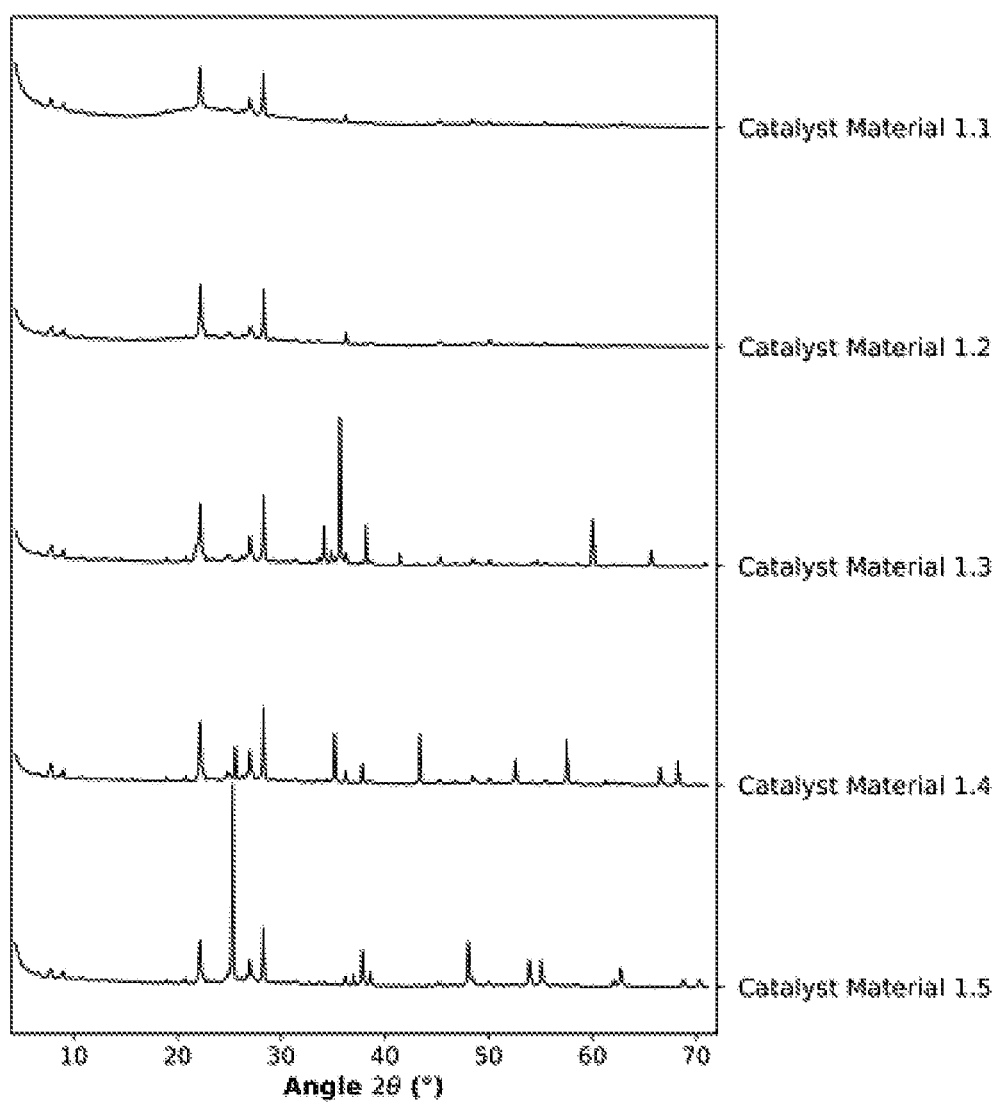
FIG. 10 shows XRD spectra for catalyst materials 1.1-1.4, and 1.6.

FIG. 10. Plots of XRD spectra for catalyst materials 1.1, 1.2, 1.3, 1.4, and 1.5. As can be seen in the figure, the characteristic pattern as changed as a result of the addition of support/carrier materials. The key peaks near 22.2°, 26.7°, and 28.3° are still visible, as are the peaks near 7.9° and 9.0°. Comparison of XRD for fresh versus used catalyst materials 1.1, 1.3, and 1.4 showed minor alterations in the pattern (data not shown) and relevant peaks were still present.

FTIR

Fourier Transform Infrared Spectroscopy (FTIR) is a technique used to obtain an infrared spectrum (IR) of a solid or liquid sample by shining monochromatic light over the sample and measuring light absorbance over a range of wavelengths. The FTIR technique can be used as a fingerprinting technique, where the IR spectrum of an unknown sample is overlaid with the IR spectrum of a known sample, or it can be used to identify characteristic absorptions that represent a particular kind of molecular bond (e.g., C=O, O—H, N—H, C—H, C—O, S—O, S=O, etc.). Solid samples were prepared for FTIR scanning by a pressed KBr pellet technique. The instrument onsite is a Bruker Tensor 27 FTIR Spectrophotometer and employs a laser at operating wavelength of 633 nm.

Figure 11:
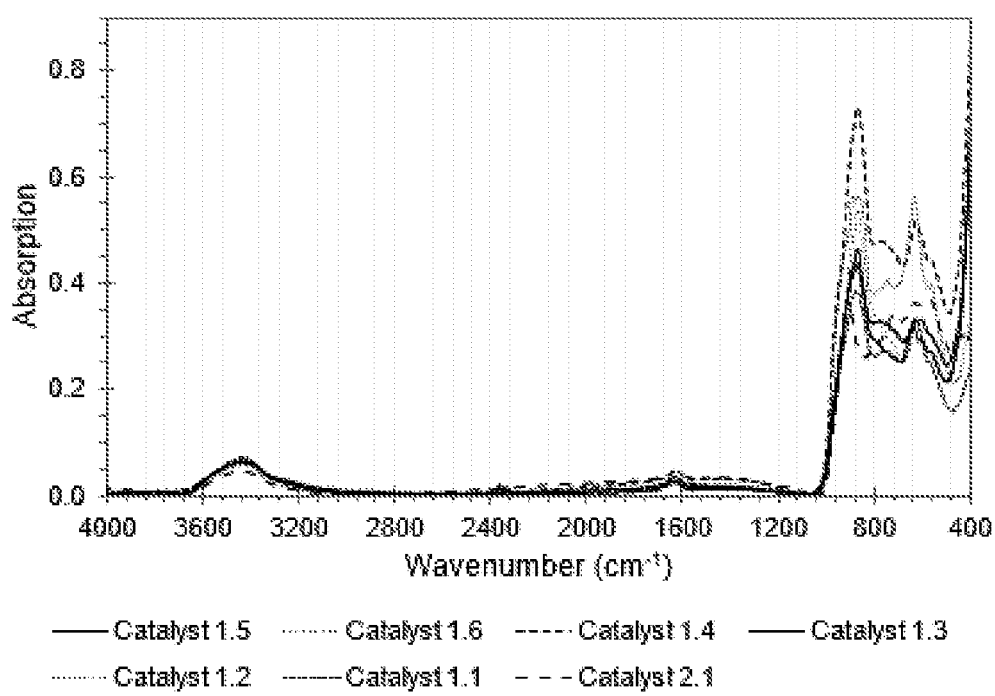
FIG. 11 shows Fourier Transform Infrared Spectroscopy (FTIR) spectra for catalysts 1.1-1.6, and 2.1.

FTIR profiles for catalysts 1.1-1.6 and 2.1 are shown in FIG. 11.

INDUSTRIAL APPLICABILITY

The present disclosure relates to a catalyst useful for oxidative dehydrogenation of ethane. The catalyst comprises molybdenum, vanadium, tellerium, and tantalum and shows good conversion and selectivity to ethylene at temperatures over 400° C.

The invention claimed is:

1. A catalyst having the formula:

$$Mo_aV_bTe_cTa_dO_x$$

wherein:
a is 1.0;
b is 0.35 to 1.0;
c is 0.1 to 1.0;
d is 0.06 to 1.0; and
x is a number to at least satisfy the valence of the catalyst; and
wherein the amorphous content of the catalyst is 30 wt. % to 50 wt. %.

2. The catalyst of claim 1, wherein:
b is 0.35 to 0.75
c is 0.1 to 0.2; and
d is 0.06 to 0.15.

3. The catalyst of claim 1, wherein:
b is 0.45 to 0.7;
c is 0.14 to 0.18; and
d is 0.06 to 0.1.

4. The catalyst of claim 1, wherein the catalyst has the formula:

$$Mo_1V_{0.39-0.49}Te_{0.12-0.17}Ta_{0.06-0.15}O_x.$$

5. The catalyst of claim 1, wherein the amorphous content of the catalyst is 30 wt. % to 40 wt. %.

6. The catalyst of claim 1, wherein the amorphous content of the catalyst is 33 wt. % to 36 wt.

7. The catalyst of claim 1, having an X-ray powder diffraction pattern comprising peaks at ° 2θ values of 22.2±0.2, 26.7±0.2, and 28.3±0.2.

8. The catalyst of claim 1, having an X-ray powder diffraction pattern comprising peaks at ° 2θ values of 7.9±0.2, 9.0±0.2, 22.2±0.2, 23.0±0.2, 25.0=0.2, 26.7±0.2, and 28.3±0.2.

9. A catalyst material comprising the catalyst of claim 1 and a catalyst support or carrier.

10. The catalyst material of claim 9, wherein the catalyst support or carrier is selected from the group consisting of precipitated synthetic silica, fumed synthetic silica, silica-alumina, α-alumina, and anatase titania.

11. The catalyst material of claim 9, wherein the catalyst support or carrier is precipitated synthetic silica.

12. A process for the oxidative dehydrogenation of ethane, the process comprising contacting a gaseous feed comprising ethane and oxygen with a catalyst in a reactor to produce an effluent comprising ethylene, wherein the catalyst has the formula:

$$Mo_aV_bTe_cTa_dO_x$$

wherein:
a is 1.0;
b is 0.35 to 1.0;

c is 0.1 to 1.0;
d is 0.06 to 1.0; and
x is a number to at least satisfy the valence of the catalyst; and wherein the amorphous content of the catalyst is 30 wt. % to 50 wt. %.

13. The process of claim 12, wherein:
b is 0.35 to 0.75
c is 0.1 to 0.2; and
d is 0.06 to 0.15.

14. The process of claim 12, wherein the catalyst has the formula:

$Mo_1V_{0.39-0.49}Te_{0.12-0.17}Ta_{0.06-0.15}O_x$.

15. The process of claim 12, wherein the amorphous content of the catalyst is 30 wt. % to 40 wt. %.

16. The process of claim 12, wherein the catalyst has an ethane conversion of 50 mol. % or more and an ethylene selectivity of 90% or more at a temperature of from 350° C. to 475° C.

17. The process of claim 12, wherein the catalyst has an ethane conversion of 50 mol. % or more and an ethylene selectivity of 90% or more at a temperature of from 400° C. to 450° C.

18. The process of claim 12, wherein the catalyst has an ethane conversion of 50 mol. % or more and an ethylene selectivity of 90% or more at a temperature of from 350° C. to 475° C. for at least 110 hours.

19. The process of claim 18, wherein the catalyst has an ethane conversion of 50 mol. % or more and an ethylene selectivity of 90% or more which at a temperature of from 400° C. to 450° C. or for at least 110 hours.

\* \* \* \* \*